(12) United States Patent
Tullis et al.

(10) Patent No.: US 6,727,364 B2
(45) Date of Patent: Apr. 27, 2004

(54) TRIAZOLE COMPOUNDS USEFUL IN TREATING DISEASES ASSOCIATED WITH UNWANTED CYTOKINE ACTIVITY

(75) Inventors: Joshua Spector Tullis, Broomfield, CO (US); John Charles Van Rens, Cincinnati, OH (US); Michael Philip Clark, Loveland, OH (US); Benjamin Eric Blass, Cincinnati, OH (US); Michael George Natchus, Alpharetta, GA (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/133,044

(22) Filed: Apr. 24, 2002

(65) Prior Publication Data

US 2003/0013712 A1 Jan. 16, 2003

Related U.S. Application Data

(60) Provisional application No. 60/287,639, filed on Apr. 30, 2001.

(51) Int. Cl.$^7$ .................. C07D 401/04; A61K 31/4196; A61P 19/02; A61P 9/04
(52) U.S. Cl. ..................... 546/268.4; 514/340
(58) Field of Search ........................ 546/268.4; 514/340

(56) References Cited

FOREIGN PATENT DOCUMENTS

| GB | 1 422 047 | 1/1976 |
|---|---|---|
| WO | WO 95/13067 | 5/1995 |
| WO | WO 97/47618 | 12/1997 |
| WO | WO 99/03837 | 1/1999 |
| WO | WO 00/10563 | 3/2000 |
| WO | WO 00/26209 | 5/2000 |
| WO | WO 01/12189 | 2/2001 |
| WO | WO 01/12621 A1 | 2/2001 |

OTHER PUBLICATIONS

Dinarello, "Interleukin–1" *Reviews of Infectious Diseases*, vol. 6, No. 1, pp. 51–95 (Jan.–Feb. 1984).
Maini, R., et al., "Infliximab (chimeric anti–tumour necrosis factor monoclonal antibody) verses placebo in rheumatoid arthritis patients receiving concomitant methotrexate: A randomized phase III trial", *The Lancet*, vol. 354, pp. 1932–1939 (Dec. 1999).
Weinblatt, M.E., et al., "A Trial of Etanercept in Patients with Rheumatoid Arthritis receiving Methotrexate", *The New England Journal of Medicine*. vol. 340, No. 4, pp. 253–259 (Jan. 1999).
Pelletier, J., et al., "Coordinate Synthesis of Stromelysin Interleukin–1, and Oncogene Proteins in Experimental Osteoarthritis: An Immunohistochemical Study", *American Journal of Pathology*, vol. 142, No. 1, pp. 95–105 (Jan. 1993).
Farahat, M.N. et al., "Cytokine expression in synovial membranes of patients with rheumatoid arthritis and osteoarthritis", *Annals of the Rheumatic Diseases*; vol. 52, pp. 870–875 (Aug. 1993).
Tiku, K., et al., "Articular Chondrocytes Secrete IL–1, Express Membrane IL–1 Inhibitory Activity", *Cellular Immunology*, vol. 140, pp. 1–20 (1992).
Webb, G. et al., "Chondrocyte tumor necrosis factor receptors and focal loss of cartilage in Osteoarthritis", *Osteoarthritis and Cartilage*; 5, pp. 427–437 (1997).
Westacott, C.I., et al., "Tumor necrosis factor alpha can contribute to focal loss of cartilage in Osteoarthritis", *Osteoarthritis and Cartilage*; 8, pp. 213–221 (2000).
McDaniel, M., et al., "Cytokines and Nitric Oxide in Islet Inflammation and Diabetes" *Nitric Oxide and Diabetes*, pp. 24–32 (1996).
Stack, A. et al., "Randomised controlled trial of CDP571 antibody to tumor necrosis factor in Crohn's disease", *The Lancet*; vol. 349, pp. 521–524 (1997).
Hunter, J., et al., "Mechanisms of Disease", The New England Journal of Medicine; vol. 341, No. 17, pp. 1276–1283 (Oct. 1999).
Han, J., et al., "Regulation of MEF2 by p38 MAPK and Its Implication in Cardiomycete Biology", *Trends Cardiovasc Med*; vol. 10, pp. 19–22 (2000).
Shimamoto, A., et al., "Neuropsychological Dysfunction after Cardiac Surgury: Preoperative Evaluation of Cerebral Perfusion Reserve Using TC–99m ECD SPECT Enhanced by Axctazolamide", *Supplement II Circulation*; vol. 102, No. 18, p. II–680 (Oct. 2000).

(List continued on next page.)

*Primary Examiner*—Venkataraman Balasubramanian
(74) *Attorney, Agent, or Firm*—Richard S. Echler, Sr.

(57) ABSTRACT

The present invention relates to 4-aryl triazoles having the formula:

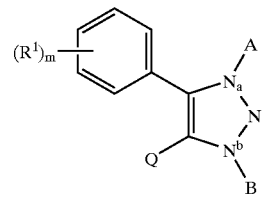

wherein $R^1$ is independently selected from the group consisting of: lower alkyl, lower alkenyl, lower alkynyl, lower heteroalkyl, lower heteroalkenyl, lower heteroalkynyl, heterocycloalkyl, heteroaryl, halo, CN, $OR^4$, $SR^4$, $S(O)R^4$, $S(O)_2R^4$, and $NR^4R^5$; and Q is has the general formula:

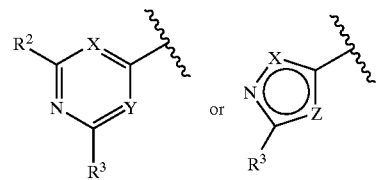

said compounds are useful in treating diseases associated with unwanted cytokine activity, inter alia, interleukin-1 (IL-1) and tumor necrosis factor (TNF) from cells.

1 Claim, No Drawings

OTHER PUBLICATIONS

Behr, T., et al., "Sustained Activation of Cardiac P38 Mitogen Activated protein Kinase in the Development of Heart Failure", *Basic Science, Abstracts from Scientific Sessions*; p. II–289 (2000).

Aukrust, P., et al., "Cytokine Network in Congestive Heart Failure Secondary to Ischemic or Idiopathic Dilated Cardiomyopathy", *The American Journal of Cardiology*; vol. 83, pp. 376–382 (Feb. 1999).

Singh, A., et al., "Inducible Nitric Oxide Synthase in Vascular Smooth Muscle Cells From Prehypertensive Spontaneously Hypertensive Rats", *The American Journal of Hypertension*, Ltd.; vol. 9, No. 9. 11 pages (Sep. 1996).

Dinarello, C., "Interleukin–1 and Interleukin–1 Receptor Antagonist", *Supplement to Nutrition*; vol. 11, No. 5, pp. 492–494 (1995).

Renzetti, L.M., et al., "Ro 45–2081, a TNF Receptor Fusion Protein, Prevents Inflammatory Responses in the Airways", *Inflammation Research*; vol. 46, Supplement 2, pp. S143–S144 (1997).

Elhage, R., et al., "Differential Effects of Interleukin–1 Receptor Antagonist and Tumor Necrosis Factor Binding Protein on Fatty–Streak Formation in Apolipoprotein E–Deficient Mice", *Circulation*: vol. 97, pp. 242–244 (1998).

Howells, GL "Cytokine Networks in Destructive Periodontal Disease", *Oral Diseases*; vol. 1, pp. 266–270 (1995).

Beisel, W. "Herman Award Lecture, 1995: Infection–induced malnutrition–from Cholera to Cytokines", *The American Journal of Clinical Nutrition*; vol. 62, pp. 813–819 (1995).

Holden, R., J., et al., "The Role of Tumor Necrosis Factor–α in the Pathogenesis of Anorexia and Bulimia Nervosa, Cancer Cachexia and Obesity", *Medical Hypothesis*: vol. 47, pp. 423–438 (1996).

Salituro, F., et al., "Inhibitors of p38 MAP Kinase: Therapeutic Intervention in Cytokine–Mediated Diseases", *Current Medicinal Chemistry*; vol. 6, pp. 807–823 (1999).

Foster, M., et al., "Potential of p38 Inhibitors in the Treatment of Rheumatoid Arthritis", *Drug News Perspect*; vol. 13, No. 8, pp. 488–497 (Oct. 2000).

Adams, J. et al., "Pyrimidinylimidazole Inhibitors of CSBP/P38 Kinase Demonstrating Decreased Inhibition of Hypatic Cytochrome P450 Enzymes", *Bioorganic and Medicinal Chemistry Letters*; vol. 8, pp. 3111–3116 (1998).

TRIAZOLE COMPOUNDS USEFUL IN TREATING DISEASES ASSOCIATED WITH UNWANTED CYTOKINE ACTIVITY

CROSS REFERENCE TO RELATED APPLICATIONS

This application claims priority under Title 35, United States Code 119(e) from Provisional Application Ser. No. 60/287,639, filed Apr. 30, 2001.

TECHNICAL FIELD

The present invention is directed to certain triazole compounds that inhibit the release of inflammatory cytokines such as interleukin-1 (IL-1) and tumor necrosis factor (TNF) from cells. The compounds of the invention, therefore, are useful in treating diseases involving unwanted cytokine activity.

BACKGROUND

Many cytokine-mediated diseases and conditions are associated with excessive or unregulated production or activity of one or more cytokines such as interleukin 1 (IL-1), tumor necrosis factor (TNF), interleukin 6 (IL-6) and interleukin 8 (IL-8). IL-1 and TNF are important proinflammatory cytokines, which along with several other related molecules, mediate inflammatory cellular response in a wide variety of diseases and conditions. Proinflammatory cytokines such as IL-1 and TNF stimulate other inflammatory mediators such as nitric oxide, cyclooxygenase-2, matrix metalloproteinases. The inhibition of these cytokines is consequently both directly and indirectly beneficial in controlling, reducing and alleviating many of these disease states.

Elevated levels of proinflammatory cytokines are implicated in many disease states, including rheumatoid arthritis (Dinarello, C. A., et al. 1984, *Rev. Infect. Disease* 6:51; Maini, R. E. 1999, *The Lancet* 354:1932; Weinblatt, M. E. 1999, *New Eng. J. Med.* 340:253), osteoarthritis (Pelletier and Pelletier 1989, *J. Rheum.* 16:19; Pelletier, et al. 1993, *Am. J. Path.* 142:95; Farahat, et al. 1993, *Ann. Rheum. Dis.* 52:870; Tiku, et al. 1992, *Cell Immunol.* 140:1; Webb, et al. 1997, *O. & C.* 5:427; Westacott, et al. 2000, *O. & C.* 8:213), diabetes (McDaniel, et al. 1996, *Proc. Soc. Exp. Biol. Med.* 211:24), HIV/AIDS (Kreuzer, et al. 1997, *Clin. Exp. Immunol.* 45:559), acute and chronic inflammatory diseases, such as the inflammatory reaction induced by endotoxin or inflammatory bowel disease, Crohn's disease and ulcerative colitis (Rankin, E. C. C., et al. 1997, *British J. Rheum.* 35:334; Stack, W. A., et al. 1997, *The Lancet* 349:521); congestive heart failure Han et al. 2000, *Trends Cardiovasc. Med.* 10:19; Hunter et al. 1999, *N. Engl. J. Med.* 341:1276;Behr et al. 2000, *Circ.* 102:II-289;Shimamoto et al. 2000, *Circ:* 102:II-289; Aukrust et al. 1999, *Am. J. Cardiol.* 83:376, hypertension (Singh, et al. 1996 *J. Hypertension* 9:867), chronic obstructive pulmonary disease, septic shock syndrome (Dinarello, C. A. 1995, *Nutrition* 11:492), tuberculosis, adult respiratory distress, asthma (Renzetti, et al. *Inflammation Res.* 46:S143), atherosclerosis (Elhage, et al. 1998, *Circulation* 97:242), muscle degeneration, periodontal disease (Howells 1995, *Oral Dis.* 1:266), cachexia, Reiter's syndrome, gout, acute synovitis, eating disorders including anorexia and bulimia nervosa (Holden, et al. 1996, *Med. Hypothesis* 47:423), fever, malaise, myalgia and headaches (Beisel 1995 *Am. J. Clin. Nutr.* 62:813). Inhibition of proinflammatory cytokine production, therefore, may offer the opportunity to treat or prevent a wide range of diseases and conditions involving elevated levels of proinflammatory cytokines.

Numerous small molecule inhibitors of cytokine production have been disclosed. (See Salituro, F. G. et al. 1999, 6, 807–823 and references cited therein). In particular, 1,2,4-triazoles (WO 00/10563 and WO 97/47618), isoxazoles (WO 01/12621), and imidazoles (WO 00/26209, WO 99/03837 and references therein) have been disclosed. However, certain liver toxicities, such as increased liver size and increased cytochrome P450 induction, have recently been reported (Foster, M. L. et al., *Drug News Perspect,* 2000, 13(8), 488–497 and Adams, J. L. et al., *Bioorg Med Chem Lett,* 1998, 8, 3111–3116). In light of the this potential toxicity and the risks associated with developing human drugs, a continuing need exists for potent new small molecule inhibitors of cytokine production with improved pharmacokinetic and safety profiles.

SUMMARY OF THE INVENTION

The invention provides compounds which are potent cytokine inhibitors and which are effective in treating conditions characterized by excess activity of these enzymes. In particular, the present invention is directed to compounds having a structure according to Formula (I):

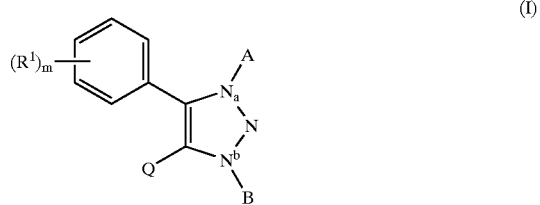

wherein $R^1$, m, A, a, B, b, and Q are defined herein.

The invention also includes optical isomers, diasteriomers, and enantiomers of the structure above, and pharmaceutically-acceptable salts thereof.

The compounds of the present invention are useful for the treatment of diseases and conditions which are characterized by unwanted cytokine activity. Accordingly, the invention further provides pharmaceutical compositions comprising these compounds. The invention still further provides methods of treatment for diseases associated with unwanted cytokine activity using these compounds or the compositions comprising them.

All documents cited are, in relevant part, incorporated herein by reference; the citation of any document is not to be construed as an admission that it is prior art with respect to the present invention.

DETAILED DESCRIPTION OF THE INVENTION

The invention is directed to a novel group of compounds which are potent inhibitors of cytokines and which are effective in treating conditions characterized by excess activity of these enzymes.

Terms and Definitions

"Alkenyl" is a monovalent hydrocarbon chain having 2 to 18 carbon atoms, preferably 2 to 12, more preferably 2 to 6 carbon atoms and at least one (preferably only one) carbon-carbon double bond. Alkenyl groups may be straight or branched. Preferred branched alkenyl groups have one or two branches, preferably one branch. Alkenyl groups may be unsubstituted or substituted with from 1 to 4 substituents.

Preferred substituted alkenyl groups have 1 to 3 substituents unless otherwise specified. Alkenyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkenyl group substituents include halo, OH, alkoxy, aryloxy (e.g., phenoxy), aryl (e.g., phenyl), heteroaryl, heterocycloalkyl, amino, and keto. The term "lower alkenyl" refers to an alkenyl group having from 2 to 6, preferably from 2 to 4, carbon atoms.

"Alkyl" is a monovalent saturated hydrocarbon chain having 1 to 18 carbon atoms, preferably 1 to 12, more preferably 1 to 6 carbon atoms. Alkyl groups may be straight or branched. Preferred branched alkyl groups have one or two branches, preferably one branch. Alkyl groups may be unsubstituted or substituted with from 1 to 4 substituents. Preferred substituted alkyl groups have 1 to 3 substituents unless otherwise specified. Alkyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkyl group substituents include halo, OH, alkoxy, aryloxy (e.g., phenoxy), aryl (e.g., phenyl), heteroaryl, heterocycloalkyl, amino, and keto. The term "lower alkyl" refers to an alkyl group having from 1 to 6, preferably from 1 to 4, carbon atoms.

"Alkoxy" refers to the group —OR where R is alkyl, alkenyl, alkynyl, heteroalkyl, heteroalkenyl, heteroalkynyl, cycloalkyl, cycloalkenyl, or heterocycloalkyl. Preferred alkoxy groups include methoxy, ethoxy, and iso-propoxy.

"Alkynyl" is a monovalent hydrocarbon chain having 2 to 18 carbon atoms, preferably 2 to 12, more preferably 2 to 6 carbon atoms and at least one (preferably only one) carbon-carbon triple bond. Alkynyl groups may be straight or branched. Preferred branched alkynyl groups have one or two branches, preferably one branch. Alkynyl groups may be unsubstituted or substituted with from 1 to 4 substituents. Preferred substituted alkynyl groups have 1 to 3 substituents unless otherwise specified. Alkynyl group substituents include halo, OH, alkoxy, aryloxy (e.g., phenoxy), aryl (e.g., phenyl), heteroaryl, cycloalkyl, heterocycloalkyl, thioalkoxy, thioaryloxy, amino, keto, thioketo, nitro, and cyano. Preferred alkynyl group substituents include halo, OH, alkoxy, aryloxy (e.g., phenoxy), aryl (e.g., phenyl), heteroaryl, heterocycloalkyl, amino, and keto. The term "lower alkynyl" refers to an alkynyl group having from 2 to 6, preferably from 2 to 4, carbon atoms.

"Amino" refers to the group —N(R)$_2$ where each R is independently chosen from the group consisting of: hydrogen, alkyl, alkenyl, alkynyl, heteroalkyl, heteroalkenyl, heteroalkynyl, cycloalkyl, cycloalkenyl, heterocycloalkyl, aryl and heteroaryl. Preferred amino groups include NH$_2$, NHCH$_3$, and NHC(O)CH$_3$.

"Aryl" is an aromatic hydrocarbon ring system. Aryl rings are either monocyclic ring systems or fused bicyclic ring systems. Monocyclic aryl rings contain 6 carbon atoms in the ring. Monocyclic aryl rings are also referred to as phenyl rings. Bicyclic aryl rings contain from 8 to 12 carbon atoms, preferably 8 to 10 carbon atoms, more preferably 10 carbon atoms, in the ring. Bicyclic aryl rings include ring systems wherein both rings are aromatic or only one ring is aromatic. Preferred bicyclic aryl rings comprise 5-, 6- or 7-membered rings fused to 5-, 6-, or 7-membered rings. Preferred aryl rings include naphthyl, tolyl, xylyl, and phenyl. The most preferred aryl ring is phenyl. Aryl rings may be unsubstituted or substituted with from 1 to 5, preferably from 1 to 3, more preferably from 1 to 2 substituents on the ring.

Preferred aryl rings are unsubstituted or substituted with 1 or 2 substituents. Aryl rings may be substituted with halo, cyano, nitro, hydroxy, amino, alkyl, lower alkenyl, lower alkynyl, heteroalkyl, aryloxy, alkoxy, methylenedioxy [which refers to the group (—OCH$_2$O—)], thioalkoxy, thioaryloxy, or any combination thereof. Preferred aryl ring substituents include halo, cyano, amino, alkyl, heteroalkyl, aryloxy, alkoxy, methylenedioxy, thioalkoxy, thioaryloxy.

"Aryloxy" refers to the group —OR where R is aryl or heteroaryl. Preferred aryloxy groups include phenoxy and pyridinyloxy.

"Cyano" refers to the group —CN.

"Cycloalkyl" is a saturated hydrocarbon ring. Cycloalkyl rings are monocyclic, or are fused, spiro, or bridged bicyclic ring systems. Preferred cycloalkyl rings are monocyclic. Monocyclic cycloalkyl rings contain from 3 to 10 carbon atoms, preferably from 3 to 7 carbon atoms, more preferably 3, 5, or 6 carbon atoms in the ring. Bicyclic cycloalkyl rings contain from 7 to 17 carbon atoms, preferably from 7 to 12 carbon atoms, in the ring. Preferred bicyclic cycloalkyl rings comprise 5-, 6- or 7-membered rings fused to 5-, 6-, or 7-membered rings. Preferred cycloalkyl rings include cyclopropyl, cyclopentyl, and cyclohexyl. Cycloalkyl rings may be unsubstituted or substituted with from 1 to 4 substituents on the ring. Cycloalkyl group substituents include alkyl, aryl (e.g., phenyl), alkoxy, aryloxy (e.g., phenoxy), thioalkoxy, thioaryloxy, heteroaryl, heterocycloalkyl, halo, hydroxy, amino, keto, thioketo, nitro, and cyano. Preferred cycloalkyl group substituents include halo, hydroxy, alkyl, aryl (e.g., phenyl), alkoxy, aryloxy (e.g., phenoxy), heteroaryl, heterocycloalkyl, amino, and keto. More preferred cycloalkyl group substituents include hydroxy, alkyl, and alkoxy.

"Cycloalkenyl" is an unsaturated hydrocarbon ring. Cycloalkenyl rings are not aromatic and contain at least one (preferably only one) carbon-carbon double bond. Cycloalkenyl rings are monocyclic, or are fused, spiro, or bridged bicyclic ring systems. Preferred cycloalkenyl rings are monocyclic. Monocyclic cycloalkenyl rings contain from 5 to 10 carbon atoms, preferably from 5 to 7 carbon atoms, more preferably 5 or 6 carbon atoms in the ring. Bicyclic cycloalkenyl rings contain from 8 to 12 carbon atoms in the ring. Preferred bicyclic cycloalkenyl rings comprise 5-, 6- or 7-membered rings fused to 5-, 6-, or 7-membered rings. Cycloalkenyl rings may be unsubstituted or substituted with from 1 to 4 substituents on the ring. Cycloalkenyl group substituents include alkyl, aryl (e.g., phenyl), alkoxy, aryloxy (e.g., phenoxy), thioalkoxy, thioaryloxy, heteroaryl, heterocycloalkyl, halo, hydroxy, amino, keto, thioketo, nitro, and cyano. Preferred cycloalkenyl group substituents include halo, hydroxy, alkyl, alkoxy, aryloxy (e.g., phenoxy), aryl (e.g., phenyl), heteroaryl, heterocycloalkyl, amino, and keto. More preferred cycloalkyl group substituents include OH, alkyl, alkoxy, and keto.

"Halo" or "halogen" is fluoro, chloro, bromo or iodo. Preferred halo are fluoro, chloro and bromo. More preferred halo are chloro and fluoro, especially fluoro.

"Heteroalkenyl" is a monovalent chain having 3 to 18 member atoms (carbon and heteroatoms) in the chain, preferably 3 to 12, more preferably 3 to 6 member atoms and at least one (preferably only one) carbon-carbon double bond. Heteroalkenyl chains have at least one heteroatom member atom. Heteroalkenyl groups may be straight or branched. Preferred branched heteroalkenyl groups have one or two branches, preferably one branch. Heteroalkenyl groups may be unsubstituted or substituted with from 1 to 4 substituents.

Preferred substituted heteroalkenyl groups have 1 to 3 substituents unless otherwise specified. Heteroalkenyl group substituents include halo, hydroxy, alkyl, alkoxy, aryloxy (e.g., phenoxy), thioalkoxy, thioaryloxy, aryl (e.g., phenyl), heteroaryl, cycloalkyl, heterocycloalkyl, amino, keto, thioketo, nitro, and cyano. Preferred heteroalkenyl group substituents include halo, hydroxy, alkyl, alkoxy, aryloxy (e.g., phenoxy), aryl (e.g., phenyl), heteroaryl, heterocycloalkyl, amino, and keto. The term "lower heteroalkenyl" refers to a heteroalkenyl group having from 3 to 6, preferably from 3 to 4, member atoms.

"Heteroalkyl" is a monovalent saturated chain having from 2 to 18 member atoms (carbon and heteroatoms) in the chain, preferably 2 to 12, more preferably 2 to 6. Heteroalkyl chains have at least one heteroatom member atom. Heteroalkyl groups may be straight or branched. Preferred branched heteroalkyl have one or two branches, preferably one branch. Heteroalkyl chains may be unsubstituted or substituted with from 1 to 4 substituents. Preferred substituted heteroalkyl groups have 1 to 3 substituents unless otherwise specified. Heteroalkyl group substituents include aryl (e.g., phenyl), alkoxy, aryloxy (e.g., phenoxy), thioalkoxy, thioaryloxy, heteroaryl, cycloalkyl, heterocycloalkyl, halo, hydroxy, amino, keto, thioketo, nitro, and cyano. Preferred heteroalkyl group substituents include aryl (e.g., phenyl), alkoxy, aryloxy (e.g., phenoxy), heteroaryl, heterocycloalkyl, halo, hydroxy, amino, and keto. The term "lower heteroalkyl" refers to a heteroalkyl group having from 2 to 6, preferably from 2 to 4, member atoms.

"Heteroalkynyl" is a monovalent chain having 3 to 18 member atoms (carbon and heteroatoms) in the chain, preferably 3 to 12, more preferably 3 to 6 member atoms and at least one (preferably only one) carbon-carbon triple bond. Heteroalkynyl chains have at least one heteroatom member atom. Heteroalkynyl groups may be straight or branched. Preferred branched heteroalkynyl groups have one or two branches, preferably one branch. Heteroalkynyl groups may be unsubstituted or substituted with from 1 to 4 substituents. Preferred substituted heteroalkynyl groups have 1 to 3 substituents unless otherwise specified. Heteroalkynyl group substituents include alkyl, aryl (e.g., phenyl), alkoxy, aryloxy (e.g., phenoxy), heteroaryl, cycloalkyl, heterocycloalkyl, halo, hydroxy, amino, keto, thioketo, nitro, and cyano. Preferred heteroalkynyl group substituents include alkyl, aryl (e.g., phenyl), alkoxy, aryloxy (e.g., phenoxy), heteroaryl, heterocycloalkyl, halo, hydroxy, amino, and keto. The term "lower heteroalkynyl" refers to a heteroalkynyl group having from 3 to 6, preferably from 3 to 4, member atoms.

"Heteroaryl" is an aromatic ring containing carbon atoms and from 1 to 6 heteroatoms in the ring. Heteroaryl rings are monocyclic or fused polycyclic ring systems. Monocyclic heteroaryl rings contain from 5 to 9 member atoms (carbon and heteroatoms), preferably 5 or 6 member atoms, in the ring. Polycyclic heteroaryl rings contain 8 to 17 member atoms, preferably 8 to 12 member atoms, in the ring. Polycyclic heteroaryl rings include ring systems wherein at least one ring is heteroaryl (the second ring may be aryl, heteroaryl, cycloalkyl, cycloalkenyl, or heterocycloalkyl). Preferred bicyclic heteroaryl ring systems comprise 5-, 6- or 7-membered rings fused to 5-, 6-, or 7-membered rings.

Preferred heteroaryl rings include, but are not limited to, the following rings:

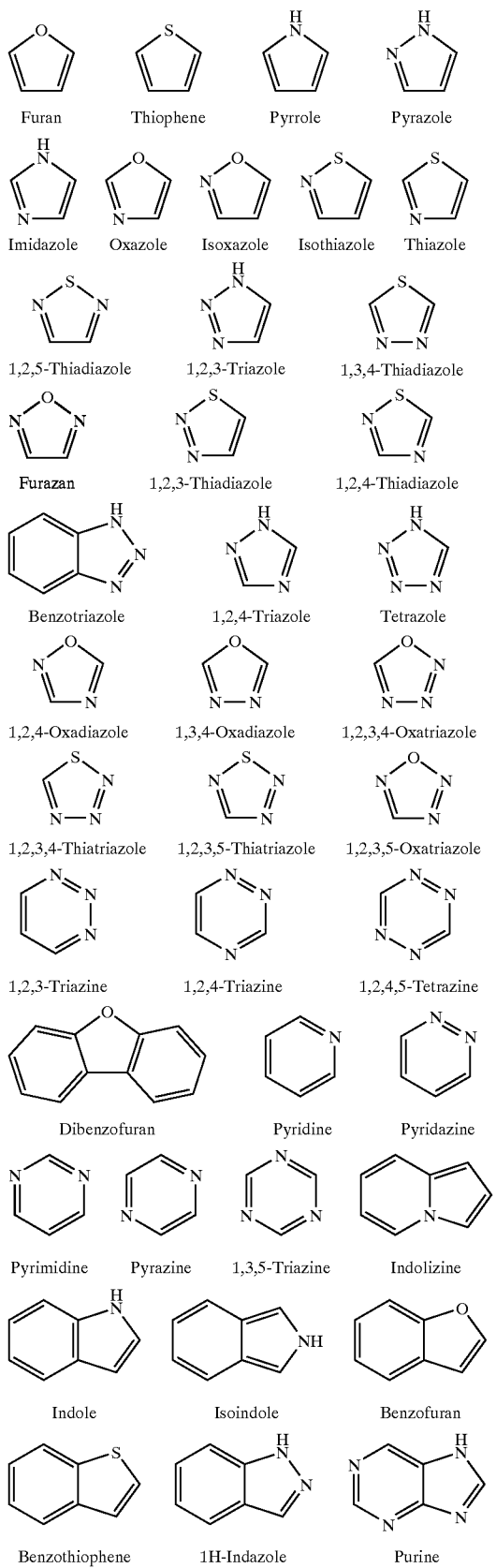

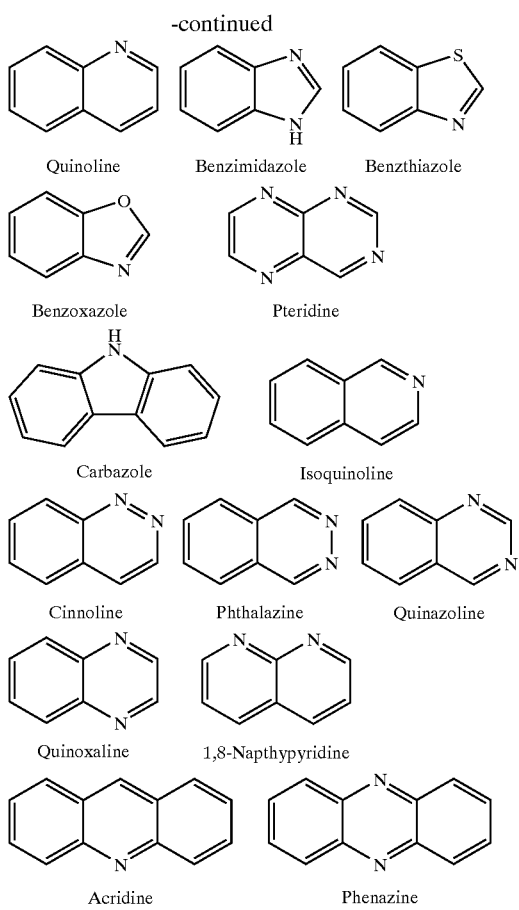

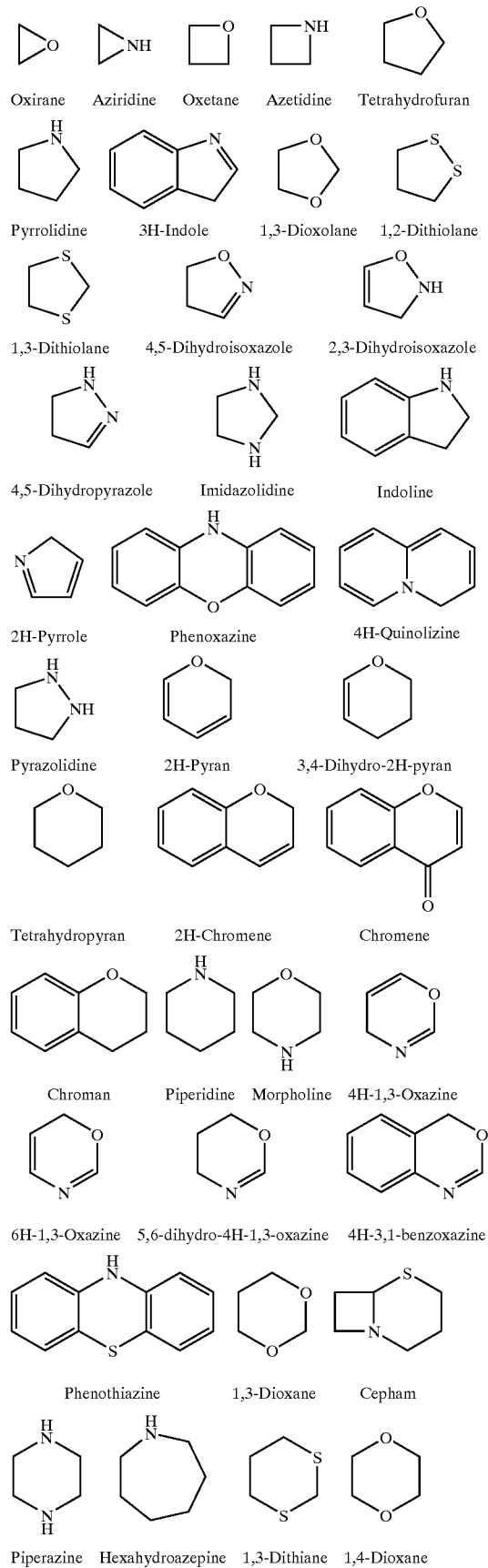

Heteroaryl rings may be unsubstituted or substituted with from 1 to 4, preferably from 1 to 3, more preferably from 1 to 2, substituents on the ring. Preferred heteroaryl rings are unsubstituted or substituted with 1 or 2 substituents. Heteroaryl rings may be substituted with halo, cyano, nitro, hydroxy, amino, alkyl, lower alkenyl, lower alkynyl, heteroalkyl, aryloxy, alkoxy, methylenedioxy, thioalkoxy, thioaryloxy, or any combination thereof. Preferred heteroaryl ring substituents include halo, cyano, amino, alkyl, heteroalkyl, aryloxy, alkoxy, methylenedioxy, thioalkoxy, thioaryloxy.

"Heteroatom" refers to a nitrogen, sulfur, or oxygen atom. Groups containing more than one heteroatom may contain different heteroatoms.

"Heterocycloalkyl" is a saturated ring containing carbon atoms and from 1 to 4, preferably 1 to 3, heteroatoms in the ring. Heterocycloalkyl rings are not aromatic. Heterocycloalkyl rings are monocyclic, or are fused, bridged, or spiro polycyclic ring systems. Monocyclic heterocycloalkyl rings contain from 3 to 9 member atoms (carbon and heteroatoms), preferably from 5 to 7 member atoms, in the ring. Polycyclic heterocycloalkyl rings contain from 7 to 17 member atoms, preferably 7 to 12 member atoms, in the ring. Preferred polycyclic heterocycloalkyl rings comprise 5-, 6- or 7-membered rings fused to 5-, 6-, or 7-membered rings. Preferred heterocycloalkyl rings include but are not limited to the following:

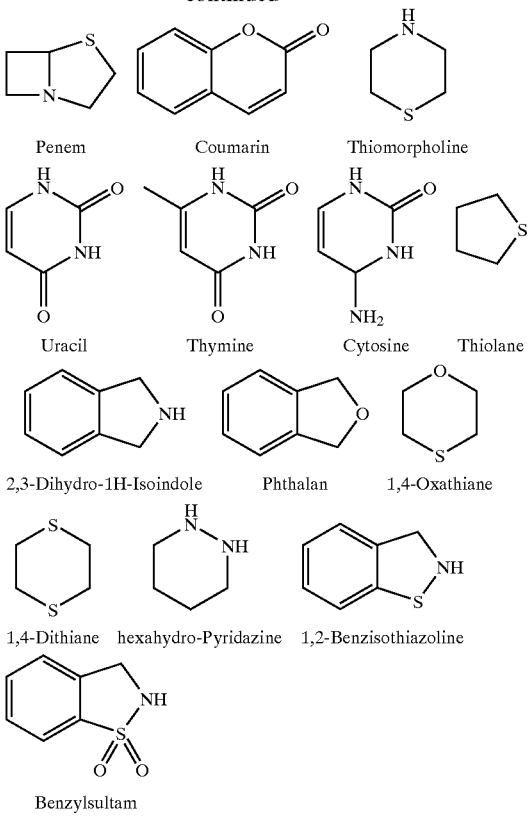

Penem    Coumarin    Thiomorpholine

Uracil    Thymine    Cytosine    Thiolane 2,3-Dihydro-1H-Isoindole    Phthalan    1,4-Oxathiane 1,4-Dithiane    hexahydro-Pyridazine    1,2-Benzisothiazoline Benzylsultam Heterocycloalkyl rings may be unsubstituted or substituted with from 1 to 4 substituents on the ring. Heterocycloalkyl group substituents include alkyl, aryl (e.g., phenyl), alkoxy, aryloxy (e.g., phenoxy), thioalkoxy, thioaryloxy, heteroaryl, cycloalkyl, halo, hydroxy, amino, keto, thioketo, nitro, and cyano. Preferred heterocycloalkyl group substituents include alkyl, aryl (e.g., phenyl), alkoxy, aryloxy (e.g., phenoxy), heteroaryl, halo, hydroxy, amino, and keto.

"Keto" refers to the group =O.

"Nitro" refers to the group —NO$_2$.

"Optical isomer", "stereoisomer", and "diastereomer" as referred to herein have the standard art recognized meanings (see, e.g., *Hawley's Condensed Chemical Dictionary*, 11th Ed.). The illustration of derivatives of the compounds of the instant invention is not intended to be limiting. The application of useful protecting groups, salt forms, etc. is within the ability of the skilled artisan.

A "pharmaceutically-acceptable salt" is a cationic salt formed at any acidic (e.g., carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there is none. For example, a chiral tartrate salt may be prepared from the compounds of the invention, and this definition includes such chiral salts.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

"Thioalkoxy" refers to the group —S(O)$_{0-2}$R where R is alkyl, alkenyl, alkynyl, heteroalkyl, heteroalkenyl, heteroalkynyl, cycloalkyl, cycloalkenyl, or heterocycloalkyl. Preferred thioalkoxy groups include methanesulfonyl.

"Thioaryloxy" refers to the group —S(O)$_{0-2}$R where R is aryl or heteroaryl. Preferred thioaryloxy groups include phenylsulfide, benzenesulfonyl and pyridinesulfonyl.

"Thioketo" refers to the group =S.

Compounds

The invention is directed to compounds of Formula (I):

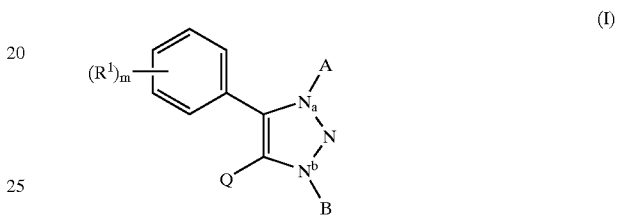

(I)

In the above structure, each $R^1$ is independently selected from the group consisting of: lower alkyl, lower alkenyl, lower alkynyl, lower heteroalkyl, lower heteroalkenyl, lower heteroalkynyl, heterocycloalkyl, heteroaryl, halo, CN, OR$^4$, SR$^4$, S(O)R$^4$, S(O)$_2$R$^4$, and NR$^4$R$^5$. Preferred $R^1$ is lower alkyl, halo, CN, OR$^4$, and NR$^4$R$^5$. More preferred $R^1$ is lower alkyl, halo, and CN.

In the above structure, m is an integer from 0 to 5. Preferred m is 0 to 3. More preferred m is 1 or 2.

In the above structure, Q is selected from the group consisting of

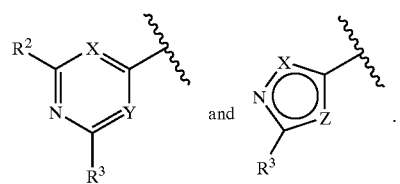

Each $R^2$ is independently selected from the group consisting of: H, alkyl, alkenyl, alkynyl, heteroalkyl, heteroalkenyl, heteroalkynyl, heterocycloalkyl, heteroaryl, halo, OH, CN, OR$^4$, SR$^4$, S(O)R$^4$, S(O)$_2$R$_4$, and NR$^4$R$^5$. Preferred $R^2$ is H, and halo. More preferred $R^2$ is H.

Provided $R^2$ is not NR$^4$R$^5$ when both Y is CR$^2$ and R$^3$ is H.

$R^3$ is selected from the group consisting of: H, alkyl, alkenyl, alkynyl, heteroalkyl, heteroalkenyl, heteroalkynyl, heterocycloalkyl, heteroaryl, halo, OH, CN, OR$^4$, SR$^4$, S(O)R$^4$, and S(O)$_2$R$^4$. Preferred $R^3$ is H, alkyl, halo, OR$^4$, SR$^4$, S(O)R$^4$, S(O)$_2$R$^4$. More preferred $R^3$ is H and OR$^4$.

X is selected from the group consisting of: CR$^2$ and N. Preferred X is CR$^2$. The most preferred X is CH.

Y is selected from the group consisting of: CR$^2$ and N. Preferred Y is CH and N.

Z is selected from the group consisting of CR$^2$, NR$^4$, O, and S.

In the above structure, A is selected from the group consisting of: nil, H, alkyl, alkenyl, alkynyl, cycloalkyl, cycloalkenyl, aryl, heteroalkyl, heteroalkenyl, heteroalkynyl, heterocycloalkyl, heteroaryl, OR$^4$, and S(O)$_2$R$^4$. Preferred A is alkyl, alkynyl, aryl, heteroalkyl, heteroalkynyl, heterocycloalkyl, heteroaryl, OR$^4$, S(O)$_2$R$^4$. More preferred A is substituted alkyl (wherein the preferred substituents are keto, alkoxy, aryloxy, amino, heteroaryl, heterocycloalkyl) and aryl.

In the above structure, a is single bond or double bond, provided that when A is nil a is double bond and when A is other than nil a is single bond.

In the above structure, B is selected from the group consisting of: nil, H, alkyl, alkenyl, alkynyl, cycloalkyl, cycloalkenyl, aryl, heteroalkyl, heteroalkenyl, heteroalkynyl, heterocycloalkyl, heteroaryl, OR$^4$, and S(O)$_2$R$^4$. Preferred B is alkyl, alkynyl, aryl, heteroalkyl, heteroalkynyl, heterocycloalkyl, heteroaryl, OR$^4$, S(O)$_2$R$^4$. More preferred B is substituted alkyl (wherein the preferred substituents are keto, alkoxy, aryloxy, amino, heteroaryl, heterocycloalkyl) and aryl.

In the above structure, b is single bond or double bond, provided that when B is nil b is double bond and when B is other than nil b is single bond.

In the above structure, one and only one of A and B is nil.

Each R$^4$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, and heteroaryl. Preferred R$^4$ is H, lower alkyl, heteroalkyl, aryl, and heteroaryl.

Each R$^5$ is independently selected from H, lower alkyl, lower alkenyl, lower alkynyl, cycloalkyl, cycloalkenyl, aryl, heteroalkyl, heteroalkenyl, heteroalkynyl, heterocycloalkyl, heterocycloalkenyl, heteroaryl, OR$^4$, and S(O)$_2$R$^4$. Preferred R$^5$ is H, lower alkyl, and S(O)$_2$R$^4$.

While alkyl, heteroalkyl, cycloalkyl, and heterocycloalkyl groups may be substituted with hydroxy and amino groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

Compound Preparation

The compounds of the invention can be prepared using conventional organic syntheses. Particularly preferred syntheses are carried out according to the following general reaction schemes, Schemes 1, 2 and 3. Schemes 1 and 2 describe general reaction schemes for making compounds of the invention wherein the "Q" substituent is a six-membered heterocyclic ring. Scheme 3 describes a general reaction scheme for making compounds of the invention wherein the "Q" substituent is a five-membered heterocyclic ring.

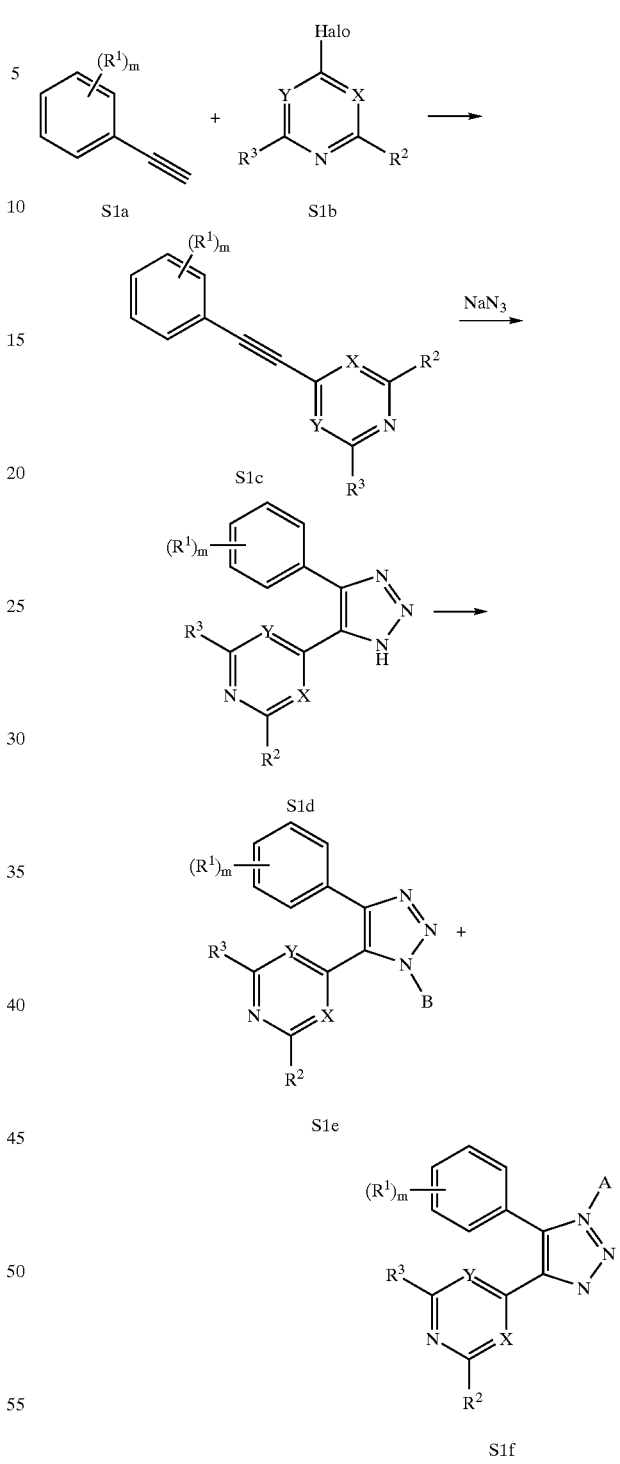

In Scheme 1, R$^1$, R$^2$, R$^3$, m, X, Y, A, B, and Q are as defined above. Alkynes of type S1a and substituted heterocycles of type S1b are either commercially available as starting material or are made from commercially available starting materials using methods known to one of ordinary skill in the art. Coupling of S1a with S1b to form alkyne S1c is accomplished using the method described by Mangalagiu, I. et al. (*Acta Chem. Scand.* 1996, 50, 914–917).

Alternatively, alkynes of type S1c can be obtained from a wide variety of commercially available substituted arylhalides and substituted 4-ethynyl-heterocycles, which in turn can be made by known methods. 3+2 Cycloaddition of alkyne S1c to give triazole S1d is performed according to a known method, but under slightly modified conditions using sodium azide to give directly the disubstituted triazole (See, Caliendo, et al. *Eur. J. Med. Chem.* 1999, 34, 719–727). Elaboration of triazole S1d is accomplished under a variety conditions to provide access to a wide variety of functionalized triazoles of type S1e and S1f. For example, acylation of S1d with acyl halides and tertiary amine base gives amides. Reaction of S1d with isocyanates or carbamoyl chlorides gives ureas. Alternatively, pretreatment of S1d with phosgene or a phosgene equivalent (e.g., triphosgene, carbonyl diimidazole) and subsequent exposure to an amine also gives ureas. Copper-mediated coupling of S1d with aryl boronic acids gives aryl amines. Reaction of S1d with sulfonyl chlorides and tertiary amine base gives sulfonamides.

In Scheme 2, $R^1$, $R^2$, $R^3$, m, X, Y, A, B, and Q are as defined above. R' and R" are each appropriate functional groups which enable the skilled artisan to functionalize the six-membered heterocycle to ultimately form a compound according to the invention. To further elaborate the triazole scaffold, R' and R" on S2d may be exchanged for a wide variety of functional groups ($R^2$ and $R^3$). In practice two approaches are used. In the first approach, triazoles of type S2d are substituted at the triazole nitrogen position as described in Scheme 1 to give S2e. When either R' or R" is —SMe, triazole S2d is oxidized specifically to either the corresponding sulfoxide or the sulphone (not shown) with several different commonly-used reagents (e.g., peracetic acid, 3-chloroperbenzoic acid, or potassium peroxymonosulfate). Either the sulfoxide or the corresponding sulphone is then displaced under nucleophilic conditions to give compounds of type S2f. In the second approach, S2d (where R' and/or R" is —SMe) is first oxidized specifically to either the sulfoxide or the sulphone. The sulfoxide or the sulphone then undergoes nucleophilic substitution (replacement of R' for $R^3$ and/or R" for $R^2$), followed by the previously described electrophilic substitution of the triazole ring to give compounds of type S2f. Using either approach, R' and/or R" may be —SMe, halo, or some other substituent capable of being displaced by $R^2$ or $R^3$. Furthermore, use of halo for Z' and/or Z" precludes the additional step of oxidizing R' and/or R" to a better leaving group.

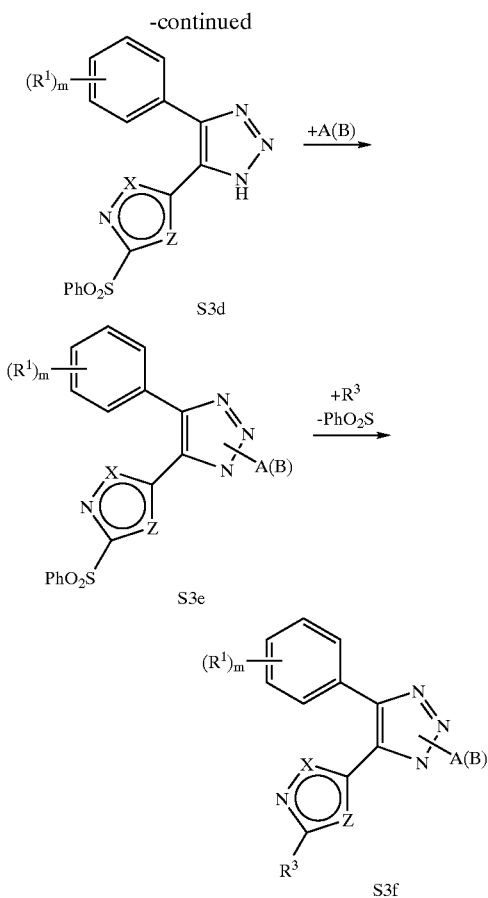

In Scheme 3, $R^1$, $R^3$, m, X, Z, A, B, and Q are as defined above. R' and R" are defined above. Alkynes of type S3a and substituted heterocycles of type S3b are either commercially available as starting material or are made from commercially available starting materials using methods known to one of ordinary skill in the art. Several substituted heterocycles of type S3b have been previously disclosed in the literature (Blass, B. E. et al. Bio. Med. Chem. Lett. 2000, 10, 1543–1545). Coupling of S3a with S3b to form alkyne S3c is accomplished as described in Scheme 1. Alternatively, alkynes of type S3c are obtained from a wide variety of commercially available substituted arylhalides and substituted 4-ethynyl-heterocycles, which in turn can be made by known methods. Oxidation to the sulphone using literature procedure is followed by 3+2 cycloaddition with sodium azide to give triazole S3d as described in Schemes 1 and 2. Functionalization of both heterocyclic rings proceeds as described in Schemes 1 and 2 to give the desired final compounds.

In Schemes 1, 2 and 3, the steps may be varied to increase the yield of the desired product. The skilled artisan will recognize the judicious choice of reactants, solvents, and temperatures is an important component in any successful synthesis. Determination of optimal conditions, solvents, reaction times, and amounts is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

EXAMPLES

The following non-limiting examples illustrate the compounds of the present invention and the methods for preparing these compounds. Compounds are analyzed using $^1$H and $^{13}$C NMR, elemental analysis, mass spectra and/or infrared spectra, as appropriate.

All solvents are purchased as the appropriate grade, and reactions are performed under an inert nitrogen atmosphere, unless otherwise noted. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

MeOH: methanol
EtOAc: ethylacetate
Ph: phenyl
DCE: 1,2-dichloroethane
DMA: dimethylacetamide
DMF: N,N-dimethylformamide -continued d: day(s)
MCPBA: meta-chloroperbenzoic acid
LC/MS: liquid chromatography/mass spectroscopy
prep HPLC.: preparative-scale high pressure
liquid chromatography
Et$_3$N: triethylamine
Et$_2$O: diethylether
conc: concentrated
TLC: thin layer chromatography
Ac: acetate
h: hour(s)
min: minute(s)

Example 1

4-(4-Fluorophenyl)-5-pyridin-4-yl-1-(thiophen-2-ylcarbonyl)-[1,2,3]triazole a) 4-(4-Fluorophenylethynyl)-pyridine

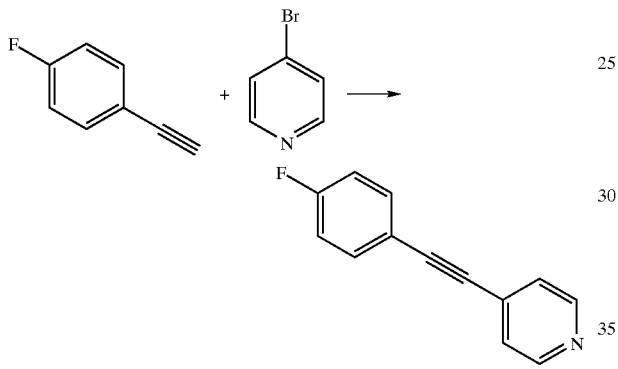

Commercially-available 1-ethynyl-4-fluorobenzene and 4-bromopyridine are reacted according to published procedure (Nangalagiu, I. et al. *Acta Chem. Scand.* 1996, 50, 914–917) to give the desired alkyne 1a as a brown solid. Using substantially the same procedure, substituting the appropriate starting material, many other alkyne intermediates can be made. The following intermediates identified in Table 1 are prepared according to the method described immediately above substituting the appropriate starting materials.

TABLE 1

| Example | Structure |
|---|---|
| 1b | F—⌬—≡—⌬(pyrimidine-SMe) |
| 1c | F—⌬—≡—⌬(pyrimidine-Cl) |
| 1d | Cl—⌬—≡—⌬(pyrimidine-Cl) |
| 1e | F$_3$C—⌬—≡—⌬(pyrimidine-Cl) |
| 1f | 2,4-F$_2$-C$_6$H$_3$—≡—⌬(pyrimidine-SMe) |
| 1g | 2,4-F$_2$-C$_6$H$_3$—≡—⌬(pyrimidine-Cl) |
| 1h | F—⌬—≡—⌬(pyridine-F) |
| 1i | F$_3$C—⌬—≡—⌬(pyridine-F) |
| 1j | F—⌬—≡—⌬(pyrimidine-Cl) |

TABLE 1-continued

| Example | Structure |
|---------|-----------|
| 1k | 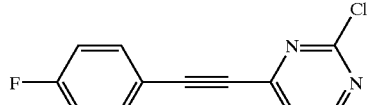 | l) 5-(4-Fluorophenyl)-4-pyridin-4-yl-[1,2,3]triazole

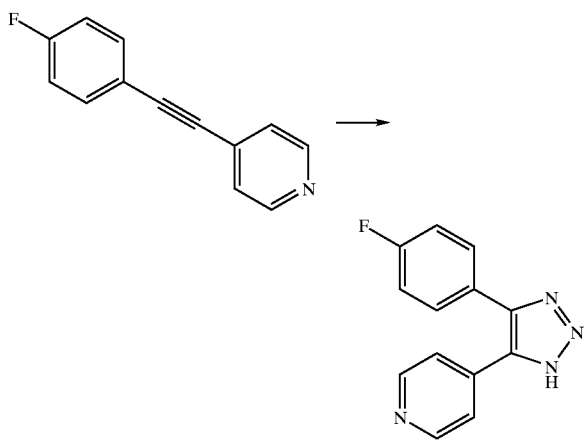

To a stirred solution of alkyne 1a (30.0 g, 0.152 mol) in DMA (500 mL) is added sodium azide (10.4 g, 0.160 mol). The reaction mixture is heated to 100° C. for 5 h until it is judged complete by the disappearance of 1a on TLC. The solution is concentrated under reduced pressure to give a semisolid residue, which is diluted with water and acidified to pH 6. The aqueous layer is then extracted with diethyl ether four times. The combined organic layers are washed with brine, dried over $MgSO_4$, filtered and conc to give a brown oil. Purification by flash chromatography (20% $CH_2Cl_2$:EtOAc) gives the desired product as a cream-colored solid.

m) 4-(4-Fluorophenyl)-5-pyridin-4-yl-1-(thiophen-2-ylcarbonyl)-[1,2,3]triazole

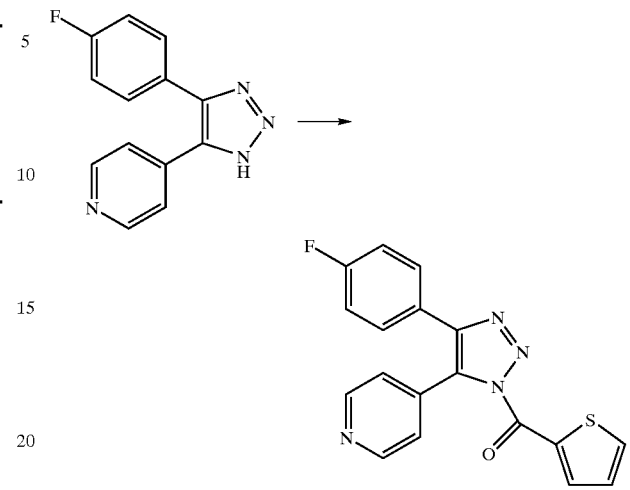

To a stirred solution of triazole 1l (60 mg, 0.25 mmol) in DCE (1.5 mL) is added triethylamine (40 μL, 0.28 mmol) followed by 2-thiophenecarbonyl chloride (30 μL, 0.28 mmol) and the reaction is allowed to stir overnight at ambient temperature. The solution is then diluted with 0.1N HCl and extracted with $CH_2Cl_2$ three times. The combined organic phases are dried over $MgSO_4$, filtered and conc to dryness. The crude product is purified by prep HPLC to give the desired product as a white solid.

Examples 2–39 are prepared using substantially the same procedures as those described in Example 1, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 2–39 are illustrated by Formula 4a and Table 2 below:

TABLE 2

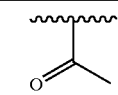

| Example | R | Compound Name |
|---------|---|---------------|
| 2 | 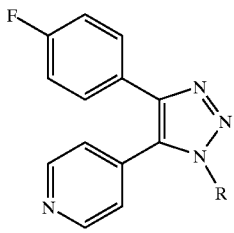 | 4-(4-Fluorophenyl)-5-pyridin-4-yl-1-methylcarbonyl-[1,2,3]triazole |

TABLE 2-continued

4a

| Example | R | Compound Name |
|---|---|---|
| 3 | (furan-2-yl)C(O)– | 4-(4-Fluorophenyl)-5-pyridin-4-yl-1-(furan-2-ylcarbonyl)-[1,2,3]triazole |
| 4 | phenyl-C(O)– | 4-(4-Fluorophenyl)-5-pyridin-4-yl-1-phenylcarbonyl-[1,2,3]triazole |
| 5 | (2-methoxyphenyl)C(O)– | 4-(4-Fluorophenyl)-5-pyridin-4-yl-1-(2-methoxyphenylcarbonyl)-[1,2,3]triazole |
| 6 | (3-methoxyphenyl)C(O)– | 4-(4-Fluorophenyl)-5-pyridin-4-yl-1-(3-methoxyphenylcarbonyl)-[1,2,3]triazole |
| 7 | (4-methoxyphenyl)C(O)– | 4-(4-Fluorophenyl)-5-pyridin-4-yl-1-(4-methoxyphenylcarbonyl)-[1,2,3]triazole |
| 8 | (2-chlorophenyl)C(O)– | 4-(4-Fluorophenyl)-5-pyridin-4-yl-1-(2-chlorophenylcarbonyl)-[1,2,3]triazole |
| 9 | (3-chlorophenyl)C(O)– | 4-(4-Fluorophenyl)-5-pyridin-4-yl-1-(3-chlorophenylcarbonyl)-[1,2,3]triazole |
| 10 | (4-chlorophenyl)C(O)– | 4-(4-Fluorophenyl)-5-pyridin-4-yl-1-(4-chlorophenylcarbonyl)-[1,2,3]triazole |
| 11 | EtO–C(O)– | 4-(4-Fluorophenyl)-5-pyridin-4-yl-1-ethoxycarbonyl-[1,2,3]triazole |

TABLE 2-continued

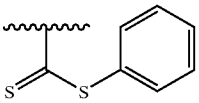

4a

| Example | R | Compound Name |
|---|---|---|
| 12 | 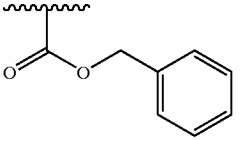 | 4-(4-Fluorophenyl)-5-pyridin-4-yl-1-(phenylthio-thiocarbonyl)-[1,2,3]triazole |
| 13 | 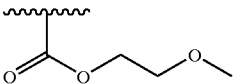 | 4-(4-Fluorophenyl)-5-pyridin-4-yl-1-phenylmethoxycarbonyl-[1,2,3]triazole |
| 14 | 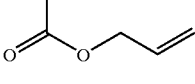 | 4-(4-Fluorophenyl)-5-pyridin-4-yl-1-(2-methoxyethoxycarbonyl)-[1,2,3]triazole |
| 15 | 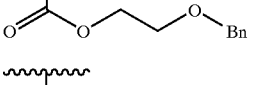 | 4-(4-Fluorophenyl)-5-pyridin-4-yl-1-allyloxycarbonyl-[1,2,3]triazole |
| 16 | 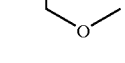 | 4-(4-Fluorophenyl)-5-pyridin-4-yl-1-[2-(phenylmethoxy)-ethoxycarbonyl)-[1,2,3]triazole |
| 17 | 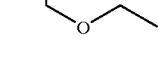 | 4-(4-Fluorophenyl)-5-pyridin-4-yl-1-methoxymethyl-[1,2,3]triazole |
| 18 | 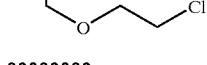 | 4-(4-Fluorophenyl)-5-pyridin-4-yl-1-ethoxymethyl-[1,2,3]triazole |
| 19 | 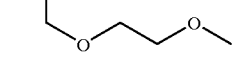 | 4-(4-Fluorophenyl)-5-pyridin-4-yl-1-(2-chloroethoxymethyl)-[1,2,3]triazole |
| 20 | 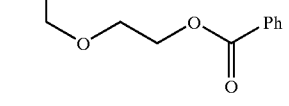 | 4-(4-Fluorophenyl)-5-pyridin-4-yl-1-[(2-methoxyethoxy)-methyl]-[1,2,3]triazole |
| 21 | 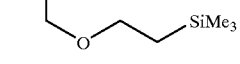 | 4-(4-Fluorophenyl)-5-pyridin-4-yl-1-[(2-(benzoyloxy)-ethoxymethyl]-[1,2,3]triazole |
| 22 | 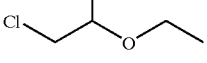 | 4-(4-Fluorophenyl)-5-pyridin-4-yl-1-[2-(trimethylsilyl)-ethoxymethyl]-[1,2,3]triazole |
| 23 | | 4-(4-Fluorophenyl)-5-pyridin-4-yl-1-(2-chloro-1-ethoxyethyl)-[1,2,3]triazole |

TABLE 2-continued

4a

| Example | R | Compound Name |
|---|---|---|
| 24 | —CH₂—O—C(O)—C(CH₃)₃ | 4-(4-Fluorophenyl)-5-pyridin-4-yl-1-pivalyloxymethyl-[1,2,3]triazole |
| 25 | —CH₂—O—CH₂—Ph | 4-(4-Fluorophenyl)-5-pyridin-4-yl-1-(phenylmethoxymethyl)-[1,2,3]triazole |
| 26 | —CH₂CH₂—O—CH₃ | 4-(4-Fluorophenyl)-5-pyridin-4-yl-1-(2-methoxyethyl)-[1,2,3]triazole |
| 27 | —CH₂CH₂—O—CH₂CH₃ | 4-(4-Fluorophenyl)-5-pyridin-4-yl-1-(2-ethoxyethyl)-[1,2,3]triazole |
| 28 | —CH₂CH₂—O—Ph | 4-(4-Fluorophenyl)-5-pyridin-4-yl-1-(2-phenoxyethyl)-[1,2,3]triazole |
| 29 | —CH₂CH₂—O—CH₂—Ph | 4-(4-Fluorophenyl)-5-pyridin-4-yl-1-[2-(phenylmethoxy)-ethyl]-[1,2,3]triazole |
| 30 | —CH₂CH₂—O—C(O)—Ph | 4-(4-Fluorophenyl)-5-pyridin-4-yl-1-[2-(phenylcarbonyloxy)-ethyl]-[1,2,3]triazole |
| 31 | —CH₂CH₂—O—CH₂CH₂—O—CH₂CH₃ | 4-(4-Fluorophenyl)-5-pyridin-4-yl-1-[2-(2-ethoxyethoxy)ethyl]-[1,2,3]triazole |
| 32 | —S(O)₂—CH₃ | 4-(4-Fluorophenyl)-5-pyridin-4-yl-1-methylsulfonyl-[1,2,3]triazole |

TABLE 2-continued

| Example | R | Compound Name |
|---|---|---|
| 33 | phenylsulfonyl | 4-(4-Fluorophenyl)-5-pyridin-4-yl-1-phenylsulfonyl-[1,2,3]triazole |
| 34 | 2-methoxyphenylsulfonyl | 4-(4-Fluorophenyl)-5-pyridin-4-yl-1-(2-methoxyphenylsulfonyl)-[1,2,3]triazole |
| 35 | 3-methoxyphenylsulfonyl | 4-(4-Fluorophenyl)-5-pyridin-4-yl-1-(3-methoxyphenylsulfonyl)-[1,2,3]triazole |
| 36 | 4-methoxyphenylsulfonyl | 4-(4-Fluorophenyl)-5-pyridin-4-yl-1-(4-methoxyphenylsulfonyl)-[1,2,3]triazole |
| 37 | 4-chlorophenylsulfonyl | 4-(4-Fluorophenyl)-5-pyridin-4-yl-1-(4-chlorophenylsulfonyl)-[1,2,3]triazole |
| 38 | 2-furansulfonyl | 4-(4-Fluorophenyl)-5-pyridin-4-yl-1-(2-furansulfonyl)-[1,2,3]triazole |

TABLE 2-continued

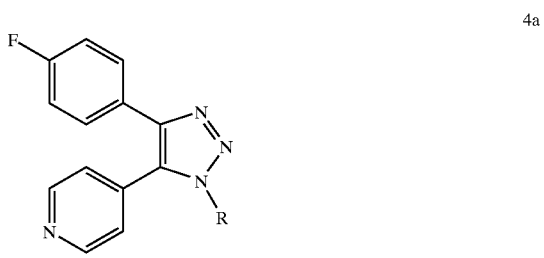

| Example | R | Compound Name |
|---|---|---|
| 39 | ~S(=O)(=O)-2-thienyl | 4-(4-Fluorophenyl)-5-pyridin-4-yl-1-(2-thiophenesulfonyl)-[1,2,3]triazole |

Example 40

4-(4-Fluorophenyl)-5-pyridin-4-yl-1-(phenylaminocarbonyl)-[1,2,3]triazole a) 4-(4-Fluorophenyl)-5-pyridin-4-yl-1-chlorocarbonyl-[1,2,3]triazole and 5-(4-Fluorophenyl)-4-pyridin-4-yl-1-chlorocarbonyl-[1,2,3]triazole

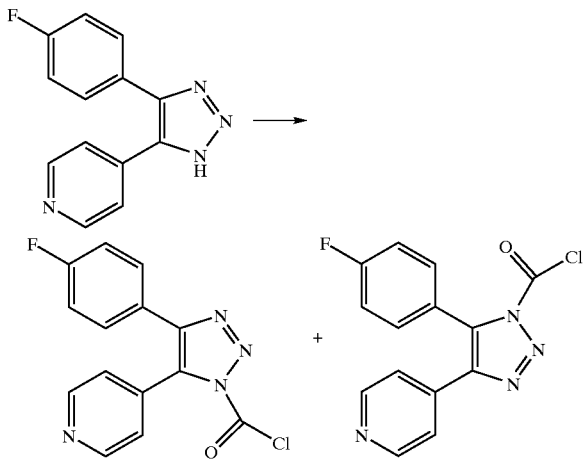

A solution of phosgene in toluene (670 μL, 1.9 mmol, 20% solution) is added to triazole 1b (90 mg, 0.38 mmol) at ambient temperature, followed by triethyamine (250 μL, 1.9 mmol). The reaction is stirred for 2 h, after which time the resulting milky orange solution is conc to dryness. The crude mixture of carbamoyl chlorides (approx. 1:1) is used without purification in the following step.

b) 4-(4-Fluorophenyl)-5-pyridin-4-yl-1-phenylaminocarbonyl-[1,2,3]triazole and 5-(4-Fluorophenyl)-4-pyridin-4-yl-1-phenylaminocarbonyl-[1,2,3]triazole

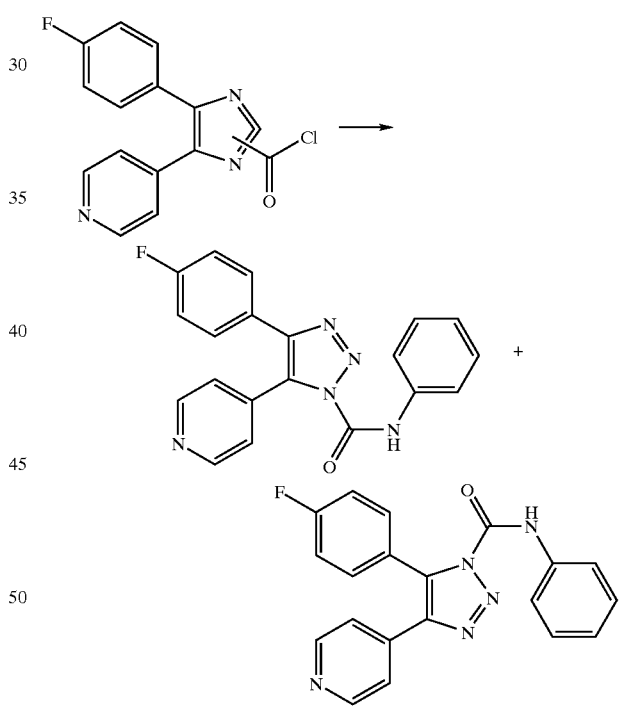

To a stirred solution of carbamoyl chloride 40a (135 mg, 0.38 mmol) in DCE (2.5 mL) is added aniline (205 μL, 2.25 mmol) and the solution is allowed to stir overnight at ambient temperature. Afterwards, the solution is diluted with 0.1N HCl and extracted with $CH_2Cl_2$ three times. The combined organic phases are dried over $MgSO_4$, filtered and conc to dryness. The crude product is purified by prep BPLC to individually give the desired products as white solids.

As an alternative approach, compounds of type 40b can also be made by reaction of an appropriate amine (e.g. aniline) with phosgene, followed by subsequent reaction with triazole 1b to give urea products (e.g. 40b).

Examples 41–54 are prepared using substantially the same procedures as those described in Example 40, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 41–54 are illustrated by Formula 4b and Table 3 below:

TABLE 3

4b

| Example | R | Compound Name |
|---------|---|---------------|
| 41 | | 4-(4-Fluorophenyl)-5-pyridin-4-yl-1-(N-ethyl-N-phenylaminocarbonyl)-[1,2,3]triazole |
| 42 | | 5-(4-Fluorophenyl)-4-pyridin-4-yl-1-(N-propyl-N-phenylaminocarbonyl)-[1,2,3]triazole |
| 43 | | 4-(4-Fluorophenyl)-5-pyridin-4-yl-1-(2,3,dihydro-indol-1-ylcarbonyl)-[1,2,3]triazole |
| 44 | | 5-(4-Fluorophenyl)-4-pyridin-4-yl-1-(2,3,dihydro-indol-1-ylcarbonyl)-[1,2,3]triazole |
| 45 | | 4-(4-Fluorophenyl)-5-pyridin-4-yl-1-(N,N-diphenylaminocarbonyl)-[1,2,3]triazole |
| 46 | | 4-(4-Fluorophenyl)-5-pyridin-4-yl-1-(carbazole-N-carbonyl)-[1,2,3]triazole |

TABLE 3-continued

4b

| Example | R | Compound Name |
|---|---|---|
| 47 | -C(O)N(CH3)2 | 4-(4-Fluorophenyl)-5-pyridin-4-yl-1-(N,N-dimethylaminocarbonyl)-[1,2,3]triazole |
| 48 | -C(O)N(Et)2 | 4-(4-Fluorophenyl)-5-pyridin-4-yl-1-(N,N-diethylaminocarbonyl)-[1,2,3]triazole |
| 49 | -C(O)N(iPr)2 | 4-(4-Fluorophenyl)-5-pyridin-4-yl-1-(N,N-di-isopropylaminocarbonyl)-[1,2,3]triazole |
| 50 | -C(O)N(nBu)2 | 4-(4-Fluorophenyl)-5-pyridin-4-yl-1-(N,N-di-n-butylaminocarbonyl)-[1,2,3]triazole |
| 51 | -C(O)-pyrrolidinyl | 4-(4-Fluorophenyl)-5-pyridin-4-yl-1-(tetrahydropyranyl-N-carbonyl)-[1,2,3]triazole |
| 52 | -C(O)-piperidinyl | 4-(4-Fluorophenyl)-5-pyridin-4-yl-1-(tetrahydrofuranyl-N-carbonyl)-[1,2,3]triazole |
| 53 | -C(O)-morpholino | 4-(4-Fluorophenyl)-5-pyridin-4-yl-1-(morpholino-N-carbonyl)-[1,2,3]triazole |
| 54 | -C(O)-piperazinyl | 4-(4-Fluorophenyl)-5-pyridin-4-yl-1-(piperidyl-N-carbonyl)-[1,2,3]triazole |

Example 55

4-(4-Fluorophenyl)-5-pyridin-4-yl-1-(N-methyl-N-phenylaminocarbonyl)-[1,2,3]triazole a) 4-(4-Fluorophenyl)-5-pyridin-4-yl-1-(N-methyl-N-phenylaminocarbonyl)-[1,2,3]triazole

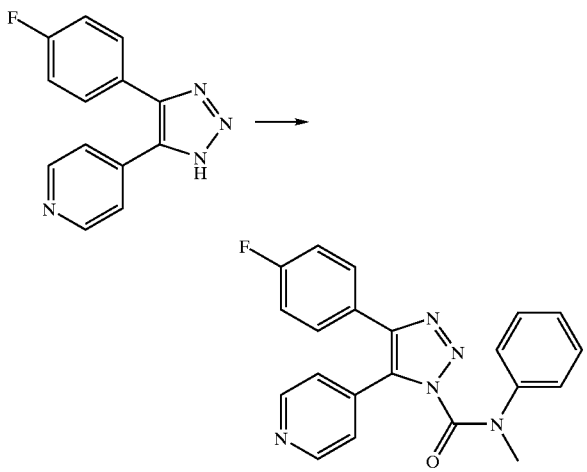

To a stirred solution of triazole 1b (90 mg, 0.38 mmol) in DCE (2.5 mL) is added N-methyl-N-phenylcarbamoyl chloride (128 mg, 0.76 mmol) and the solution is allowed to stir overnight at ambient temperature. Afterwards, the solution is diluted with 0.1N HCl and extracted wit CH$_2$Cl$_2$ three times. The combined organic phases are dried over MgSO$_4$, filtered and conc to dryness. The crude product is purified by prep HPLC to give the desired product as a white solid.

Example 56

4-(4-Fluorophenyl)-5-pyridin-4-yl-1-(phenylmethylaminocarbonyl)-[1,2,3]triazole a) 4-(4-Fluorophenyl)-5-pyridin-4-yl-1-(phenylmethylaminocarbonyl)-[1,2,3]triazole

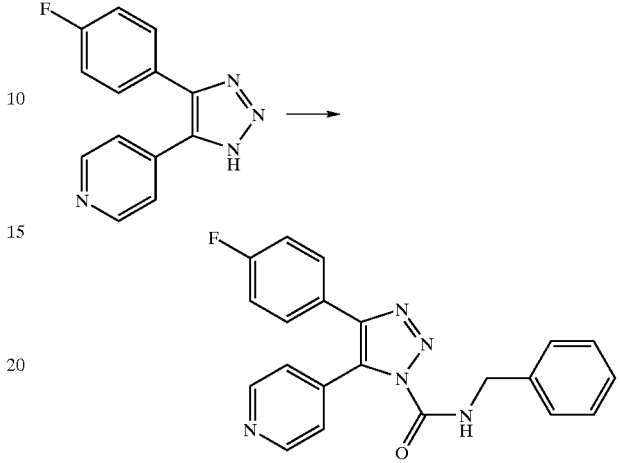

To a stirred solution of triazole 1b (200 mg, 0.83 mmol) in DCE (6 mL) is added benzylisocyanate (210 μL, 1.65 mmol) and the solution is heated to reflux overnight. Afterwards, the solution is diluted with water and extracted with CH$_2$Cl$_2$ two times. The combined organic phases are dried over MgSO$_4$, filtered and conc to dryness. The crude product is purified by prep HPLC to give the desired product as a white solid.

Examples 58–61 are prepared using substantially the same procedures as those described in Example 57, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 58–61 are illustrated by Formula 4a and Table 4 below:

TABLE 4

4a

| Example | R | Compound Name |
|---------|---|---------------|
| 58 | 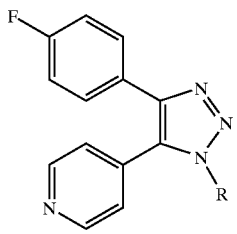 | 4-(4-Fluorophenyl)-5-pyridin-4-yl-1-[(4-methoxyphenyl)-methylaminocarbonyl]-[1,2,3]triazole |

TABLE 4-continued

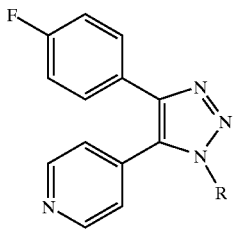

4a

| Example | R | Compound Name |
|---|---|---|
| 59 | (acetamide with 4-fluorobenzyl group) | 4-(4-Fluorophenyl)-5-pyridin-4-yl-1-[(4-chlorophenyl)-methylaminocarbonyl]-[1,2,3]triazole |
| 60 | (acetamide with 3-chloropropyl group) | 4-(4-Fluorophenyl)-5-pyridin-4-yl-1-(3-chloropropylaminocarbonyl)-[1,2,3]triazole |
| 61 | (thiazol-2-yl) | 4-(4-Fluorophenyl)-5-pyridin-4-yl-1-thiazol-2-yl-[1,2,3]triazole |

Example 62

4-(4-Fluorophenyl)-5-pyridin-4-yl-1-(phenyl)-[1,2,3]triazole a) 4-(4-Fluorophenyl)-5-pyridin-4-yl-1-(phenyl)-[1,2,3]triazole

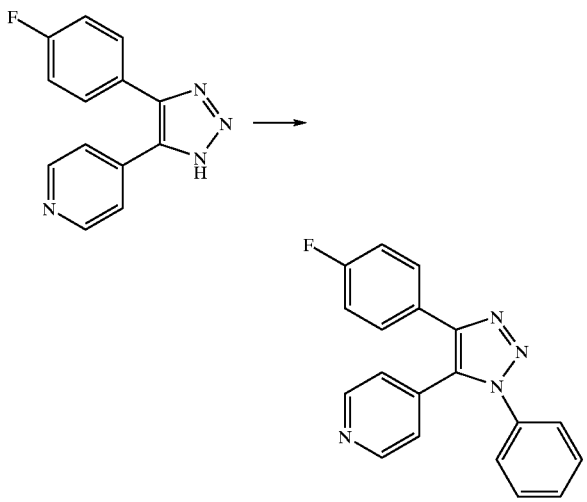

To a stirred solution of triazole 1b (100 mg, 0.42 mmol) in $CH_2Cl_2$ (6 mL) is added phenylboronic acid (100 mg, 0.83 mmol), $Cu(OAc)_2$ (110 mg, 0.63 mmol), pyridine (70 µL, 0.83 mmol) and 4 Å molecular sieves (300 mg). The reaction is stirred 72 h and then filtered through a bed of celite. The filtrate is then conc to give the crude product, which is purified by prep HPLC to give the desired product as a white solid.

Examples 63–85 are prepared using substantially the same procedures as those described in Example 62, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 63–85 are illustrated by Formula 4a and Table 5 below:

TABLE 5

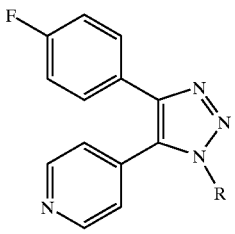

4a

| Example | R | Compound Name |
|---|---|---|
| 63 | 2-Me-phenyl | 4-(4-Fluorophenyl)-5-pyridin-4-yl-1-(2-methylphenyl)-[1,2,3]triazole |
| 64 | 4-Me-phenyl | 4-(4-Fluorophenyl)-5-pyridin-4-yl-1-(4-methylphenyl)-[1,2,3]triazole |
| 65 | 2-OMe-phenyl | 4-(4-Fluorophenyl)-5-pyridin-4-yl-1-(2-methoxyphenyl)-[1,2,3]triazole |
| 66 | 3-OMe-phenyl | 4-(4-Fluorophenyl)-5-pyridin-4-yl-1-(3-methoxyphenyl)-[1,2,3]triazole |
| 67 | 4-OMe-phenyl | 4-(4-Fluorophenyl)-5-pyridin-4-yl-1-(4-methoxyphenyl)-[1,2,3]triazole |
| 68 | 3,4-(OMe)$_2$-phenyl | 4-(4-Fluorophenyl)-5-pyridin-4-yl-1-(3,4-dimethoxyphenyl)-[1,2,3]triazole |
| 69 | 2,4-(OMe)$_2$-phenyl | 4-(4-Fluorophenyl)-5-pyridin-4-yl-1-(2,4-dimethoxyphenyl)-[1,2,3]triazole |
| 70 | benzo[1,3]dioxol-5-yl | 4-(4-Fluorophenyl)-5-pyridin-4-yl-1-(benzo[1,3]dioxol-5-yl)-[1,2,3]triazole |

TABLE 5-continued

4a

| Example | R | Compound Name |
|---|---|---|
| 71 | 4-phenyl with OCH₂CH₂OCH₃ at para | 4-(4-Fluorophenyl)-5-pyridin-4-yl-1-[4-(2-methoxyethoxy)-phenyl]-[1,2,3]triazole |
| 72 | 4-phenyl with OPh at para | 4-(4-Fluorophenyl)-5-pyridin-4-yl-1-(4-phenoxyphenyl)-[1,2,3]triazole |
| 73 | 4-phenyl with OEt at para | 4-(4-Fluorophenyl)-5-pyridin-4-yl-1-(4-ethoxyphenyl)-[1,2,3]triazole |
| 74 | 4-phenyl with OCF₃ at para | 4-(4-Fluorophenyl)-5-pyridin-4-yl-1-(4-trifluoromethoxyphenyl)-[1,2,3]triazole |
| 75 | 4-phenyl with N(CH₃)₂ at para | 4-(4-Fluorophenyl)-5-pyridin-4-yl-1-[4-(N,N-dimethylamino)-phenyl]-[1,2,3]triazole |
| 76 | 4-phenyl with Br at para | 4-(4-Fluorophenyl)-5-pyridin-4-yl-1-(4-bromophenyl)-[1,2,3]triazole |
| 77 | 4-phenyl with Cl at para | 4-(4-Fluorophenyl)-5-pyridin-4-yl-1-(4-chlorophenyl)-[1,2,3]triazole |
| 78 | 4-phenyl with F at para | 4-(4-Fluorophenyl)-5-pyridin-4-yl-1-(4-fluorophenyl)-[1,2,3]triazole |

TABLE 5-continued

| Example | R | Compound Name |
|---------|---|---------------|
| 79 | 3-fluorophenyl | 4-(4-Fluorophenyl)-5-pyridin-4-yl-1-(3-fluorophenyl)-[1,2,3]triazole |
| 80 | 4-fluoro-2-methylphenyl | 4-(4-Fluorophenyl)-5-pyridin-4-yl-1-(4-fluoro-2-methylphenyl)-[1,2,3]triazole |
| 81 | 4-(SMe)phenyl | 4-(4-Fluorophenyl)-5-pyridin-4-yl-1-(4-methylthiophenyl)-[1,2,3]triazole |
| 82 | 4-(S(O)Me)phenyl | 4-(4-Fluorophenyl)-5-pyridin-4-yl-1-(4-methylsulfinylphenyl)-[1,2,3]triazole |
| 83 | 4-(SO₂Me)phenyl | 4-(4-Fluorophenyl)-5-pyridin-4-yl-1-(4-methylsulfonylphenyl)-[1,2,3]triazole |
| 84 | 4-(CO₂Me)phenyl | 4-(4-Fluorophenyl)-5-pyridin-4-yl-1-[4-(methoxycarbonyl)-phenyl]-[1,2,3]triazole |
| 85 | 4-vinylphenyl | 4-(4-Fluorophenyl)-5-pyridin-4-yl-1-(4-vinylphenyl)-[1,2,3]triazole |

Example 86

4-(4-Fluorophenyl)-5-(2-phenoxypyrimidin-4-yl)-1-ethoxymethyl-[1,2,3]triazole a) 5-(4-Fluorophenyl)-4-(2-methylthiopyrimidin-4-yl)-1-H-[1,2,3]triazole

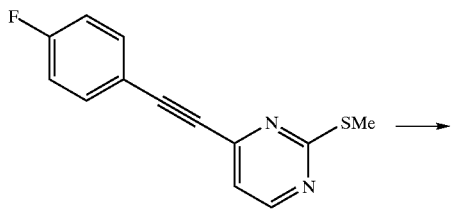

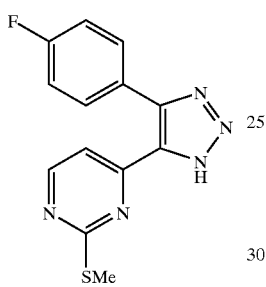

To a stirred solution of alkyne 1b (11.8 g, 48.3 mmol) in DMA (500 mL) is added sodium azide (3.14 g, 48.3 mmol). The reaction mixture is heated to 80° C. for 2 h until it is judged complete by the disappearance of 1b on TLC. The solution is diluted with pH 6.4 aqueous buffer and 1 N HCl is added dropwise to reestablish acidic pH. The aqueous layer is then extracted with ethyl acetate three times. The combined organic layers are dried over MgSO$_4$, filtered and conc to give a brown oil. Crystallization from CH$_2$Cl$_2$:Hexanes provides the desired product as a cream-colored solid.

b) 4-(4-Fluorophenyl)-5-(2-methylthiopyrimidin-4-yl)-1-ethoxymethyl-[1,2,3]triazole and 5-(4-Fluorophenyl)-4-(2-methylthiopyrimidin-4-yl)-1-ethoxymethyl-[1,2,3]triazole

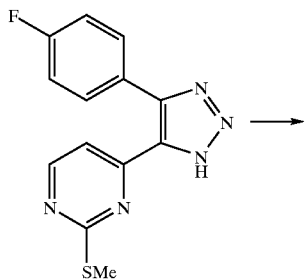

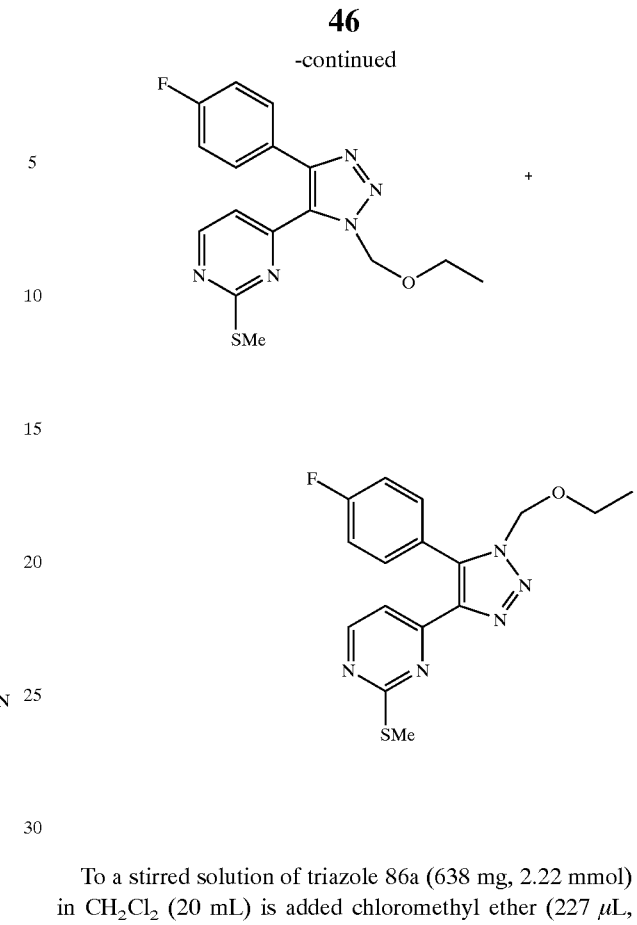

To a stirred solution of triazole 86a (638 mg, 2.22 mmol) in CH$_2$Cl$_2$ (20 mL) is added chloromethyl ether (227 μL, 2.44 mmol) and triethylamine (340 μL, 2.44 mmol). The reaction is stirred at ambient temperature for 2 h, or until TLC of the crude reaction mixture shows complete consumption of 86a. The solution is then diluted with 0.1N HCl and extracted with CH$_2$Cl$_2$ three times. The combined organic phases are dried over MgSO$_4$, filtered and conc to dryness. The crude product is purified by prep BPLC to give two separable regioisomers (approximately 1:1) as slightly yellow solids. Note: regioselectivity is dependent upon reagents and reaction conditions.

c) 4-(4-Fluorophenyl)-5-(2-methylsulfinylpyrimidin-5-yl)-1-ethoxymethyl-[1,2,3]triazole

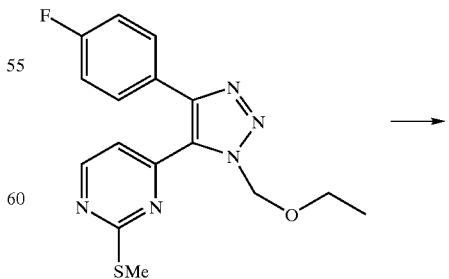

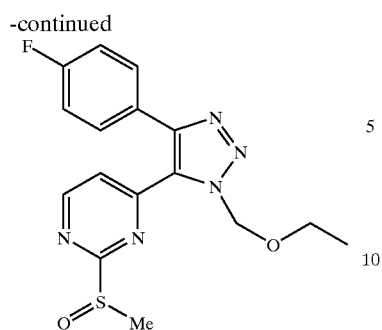

A stirred solution of triazole 86b (260 mg, 0.753 mmol) in CH₂Cl₂ (3 mL) is cooled to 0° C. and a solution of MCPBA (130 mg, 0.753 mmol) in CH₂Cl₂ (3 mL) is added. The solution becomes cloudy within minutes and the reaction is complete after 1.5 h, as determined by TLC. The reaction mixture is then diluted with EtOAc and washed consecutively with 0.5 N Na₂S₂O₃, aqueous 10% NaHCO₃ and brine. The remaining organic layer is dried over MgSO₄, filtered and conc to dryness. The crude product is purified by prep HPLC to give the desired product.

d) 4-(4-Fluorophenyl)-5-(2-methylsulfonylpyrimidin-4-yl)-1-ethoxymethyl-[1,2,3]triazole

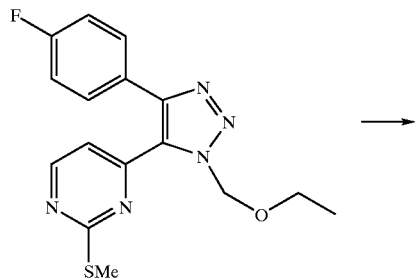

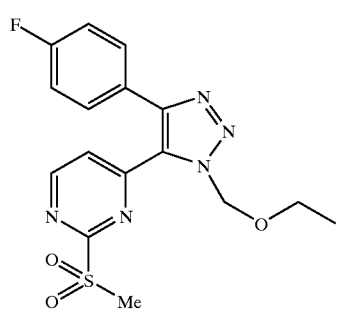

A solution of potassium peroxymonosulfate (1.07 g, 1.74 mmol) in H₂O (10 mL) is added dropwise to a stirred solution of triazole 86b (200 mg, 0.58 mmol) in MeOH (10 mL) at ambient temperature. The reaction is complete after 2 h, as determined by analytical HPLC. The reaction mixture is conc to remove MeOH. The remaining aqueous solution is diluted with aqueous 5% NaHCO₃ and extracted with EtOAc two times. The combined organic layers are dried over MgSO₄, filtered and conc to dryness. The crude product is then used without further purification.

e) 4-(4-Fluorophenyl)-5-(2-phenoxypyrimidin-4-yl)-1-ethoxymethyl-[1,2,3]triazole

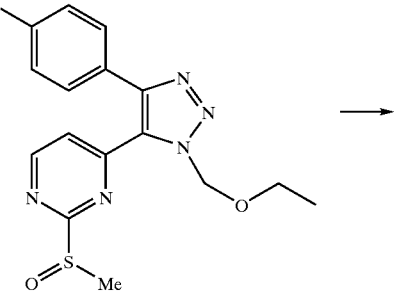

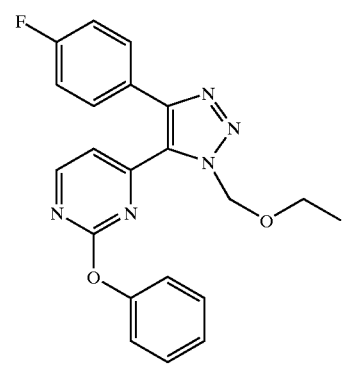

To a stirred solution of phenol (94 mg, 1.0 mmol) in tetrahydrofuran (3 mL) is added sodium hydride (60% dispersion, 50 mg, 0.75 mmol). After 5 min the suspension is transferred via syringe to a stirred solution of sulfoxide 86c (90 mg, 0.25 mmol) in tetrahydrofuran (3 mL). The reaction mixture is stirred overnight at ambient temperature, after which time the solution is diluted with H₂O and extracted with EtOAc three times. The combined organic layers are dried over MgSO₄, filtered and conc to dryness. The crude product is then purified by prep HPLC to give the desired product. As an alternative, product 86e can also be made from sulphone 86d, phenol and sodium hydride under similar conditions.

Examples 87–116 are prepared using substantially the same procedures as those described in Example 86, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 87–116 are illustrated by Formula 4c and Table 6 below:

TABLE 6

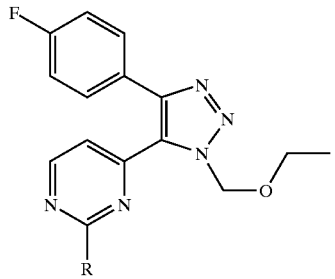

4c

| Example | R | Compound Name |
|---|---|---|
| 87 | —O—CH₃ | 4-(4-Fluorophenyl)-5-(2-methoxypyrimidin-4-yl)-1-ethoxymethyl-[1,2,3]triazole |
| 88 | —O—CH(CH₃)₂ | 4-(4-Fluorophenyl)-5-[2-(1-methylethoxy)-pyrimidin-4-yl]-1-ethoxymethyl-[1,2,3]triazole |
| 89 | —O—CH₂CH₂—O—CH₃ | 4-(4-Fluorophenyl)-5-[2-(2-methoxyethoxy)-pyrimidin-4-yl]-1-ethoxymethyl-[1,2,3]triazole |
| 90 | —O—CH₂CH₂—O—Ph | 4-(4-Fluorophenyl)-5-[2-(2-phenoxyethoxy)-pyrimidin-4-yl]-1-ethoxymethyl-[1,2,3]triazole |
| 91 | —O—(4-methylphenyl) | 4-(4-Fluorophenyl)-5-[2-(4-methylphenoxy)-pyrimidin-4-yl]-1-ethoxymethyl-[1,2,3]triazole |
| 92 | —O—(3-ethylphenyl) | 4-(4-Fluorophenyl)-5-[2-(3-ethylphenoxy)-pyrimidin-4-yl]-1-ethoxymethyl-[1,2,3]triazole |
| 93 | —O—(4-ethylphenyl) | 4-(4-Fluorophenyl)-5-[2-(4-ethylphenoxy)-pyrimidin-4-yl]-1-ethoxymethyl-[1,2,3]triazole |
| 94 | —O—(2-methoxyphenyl) | 4-(4-Fluorophenyl)-5-[2-(2-methoxyphenoxy)-pyrimidin-4-yl]-1-ethoxymethyl-[1,2,3]triazole |
| 95 | —O—(3-methoxyphenyl) | 4-(4-Fluorophenyl)-5-[2-(3-methoxyphenoxy)-pyrimidin-4-yl]-1-ethoxymethyl-[1,2,3]triazole |

TABLE 6-continued

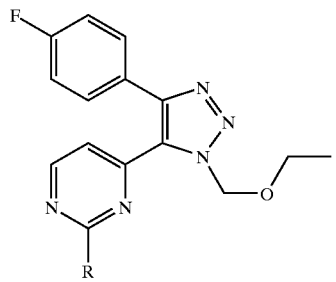

4c

| Example | R | Compound Name |
|---|---|---|
| 96 | ~O-C6H4-OMe (4-) | 4-(4-Fluorophenyl)-5-[2-(4-methoxyphenoxy)-pyrimidin-4-yl]-1-ethoxymethyl-[1,2,3]triazole |
| 97 | ~O-C6H4-CN (2-) | 4-(4-Fluorophenyl)-5-[2-(2-cyanophenoxy)-pyrimidin-4-yl]-1-ethoxymethyl-[1,2,3]triazole |
| 98 | ~O-C6H4-CN (3-) | 4-(4-Fluorophenyl)-5-[2-(3-cyanophenoxy)-pyrimidin-4-yl]-1-ethoxymethyl-[1,2,3]triazole |
| 99 | ~O-C6H4-CN (4-) | 4-(4-Fluorophenyl)-5-[2-(4-cyanophenoxy)-pyrimidin-4-yl]-1-ethoxymethyl-[1,2,3]triazole |
| 100 | ~O-C6H4-CF3 (4-) | 4-(4-Fluorophenyl)-5-[2-(4-(trifluoromethyl)-phenoxy)-pyrimidin-4-yl]-1-ethoxymethyl-[1,2,3]triazole |
| 101 | ~O-C6H4-OCF3 (3-) | 4-(4-Fluorophenyl)-5-[2-(3-(trifluoromethoxy)-phenoxy)-pyrimidin-4-yl]-1-ethoxymethyl-[1,2,3]triazole |
| 102 | ~O-C6H4-OCF3 (4-) | 4-(4-Fluorophenyl)-5-[2-(4-(trifluoromethoxy)-phenoxy)-pyrimidin-4-yl]-1-ethoxymethyl-[1,2,3]triazole |
| 103 | ~O-C6H4-NO2 (3-) | 4-(4-Fluorophenyl)-5-[2-(3-nitrophenoxy)-pyrimidin-4-yl]-1-ethoxymethyl-[1,2,3]triazole |

TABLE 6-continued

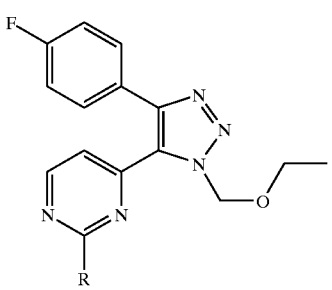

| Example | R | Compound Name |
|---|---|---|
| 104 |  | 4-(4-Fluorophenyl)-5-[2-(2-fluorophenoxy)-pyrimidin-4-yl]-1-ethoxymethyl-[1,2,3]triazole |
| 105 | 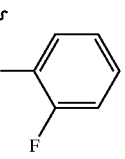 | 4-(4-Fluorophenyl)-5-[2-(3-fluorophenoxy)-pyrimidin-4-yl]-1-ethoxymethyl-[1,2,3]triazole |
| 106 |  | 4-(4-Fluorophenyl)-5-[2-(4-fluorophenoxy)-pyrimidin-4-yl]-1-ethoxymethyl-[1,2,3]triazole |
| 107 | 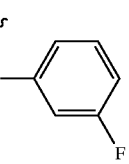 | 4-(4-Fluorophenyl)-5-[2-(2-chlorophenoxy)-pyrimidin-4-yl]-1-ethoxymethyl-[1,2,3]triazole |
| 108 |  | 4-(4-Fluorophenyl)-5-[2-(3-chlorophenoxy)-pyrimidin-4-yl]-1-ethoxymethyl-[1,2,3]triazole |
| 109 | 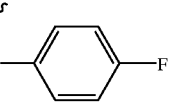 | 4-(4-Fluorophenyl)-5-[2-(4-chlorophenoxy)-pyrimidin-4-yl]-1-ethoxymethyl-[1,2,3]triazole |
| 110 |  | 4-(4-Fluorophenyl)-5-[2-(2-acetylaminophenoxy)-pyrimidin-4-yl]-1-ethoxymethyl-[1,2,3]triazole |

TABLE 6-continued

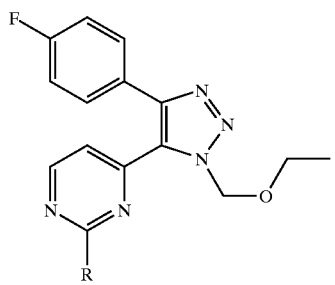

4c

| Example | R | Compound Name |
|---|---|---|
| 111 | [3-acetylamino-phenoxy group] | 4-(4-Fluorophenyl)-5-[2-(3-acetylaminophenoxy)-pyrimidin-4-yl]-1-ethoxymethyl-[1,2,3]triazole |
| 112 | [4-acetylamino-phenoxy group] | 4-(4-Fluorophenyl)-5-[2-(4-acetylaminophenoxy)-pyrimidin-4-yl]-1-ethoxymethyl-[1,2,3]triazole |
| 113 | [pyridin-4-yloxy group] | 4-(4-Fluorophenyl)-5-[2-(pyridin-4-yloxy)-pyrimidin-4-yl]-1-ethoxymethyl-[1,2,3]triazole |
| 114 | [pyrimidin-4-yloxy group] | 4-(4-Fluorophenyl)-5-[2-(pyrimidin-4-yloxy)-pyrimidin-4-yl]-1-ethoxymethyl-[1,2,3]triazole |
| 115 | [phenylthio group] | 4-(4-Fluorophenyl)-5-[2-phenylthiopyrimidin-4-yl]-1-ethoxymethyl-[1,2,3]triazole |
| 116 | [phenylmethoxy group] | 4-(4-Fluorophenyl)-5-[2-(phenylmethoxy)-pyrimidin-4-yl]-1-ethoxymethyl-[1,2,3]triazole |

Example 117

4-(4-Fluorophenyl)-5-(2-phenoxypyrimidin-4-yl)-1-ethoxymethyl-[1,2,3]triazole a) 2-(4-Fluorophenyl)-1-(2-methylthiopyrimidin-4-yl)-ethyne

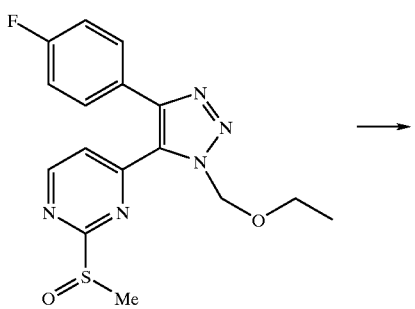

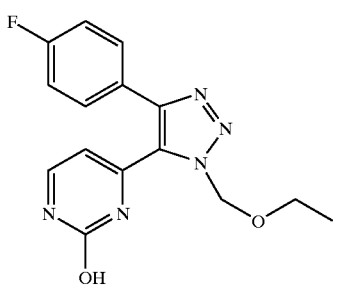

To a stirred solution of sulfoxide 86c (90 mg, 0.25 mmol) in tetrahydrofuran (3 mL) is added sodium hydroxide (50% aqueous soln, 150 μL), and the reaction mixture is allowed to stir at ambient temperature for 3 d during which time a precipitate forms. The precipitate is collected by suction filtration and washed with tetrahydrofuran. The crude product is then purified by prep HPLC to give the desired product. As an alternative, product 117 can also be made from sulphone 86d and sodium hydroxide under similar conditions.

Example 118

5-[3-(Trifluoromethyl)phenyl]-4-(2-phenoxypyrimidin-4-yl)-1-ethoxymethyl-[1,2,3]triazole a) 5-[3-(-Trifluoromethyl)phenyl]-4-(2-chloropyrimidin-4-yl)-1-H-[1,2,3]triazole

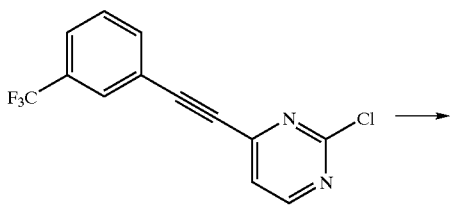

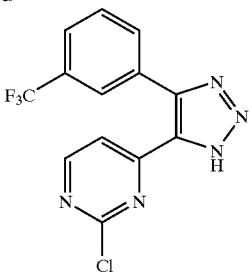

To a stirred solution of alkyne 1e (7.02 g, 24.8 mmol) in DMA (120 mL) is added sodium azide (1.61 g, 24.8 mmol). The reaction mixture is heated to 80° C. for 2 h until it is judged complete by LC/MS. The solution is diluted with pH 6.4 aqueous buffer and 1 N HCl is added dropwise to reestablish acidic pH. The aqueous layer is then extracted with ethyl acetate three times. The combined organic layers are dried over MgSO₄, filtered and conc to give a brown oil which was used without further purification b) 4-[3-(Trifluoromethyl)phenyl]-5-(2-chloropyrimidin-4-yl)-1-ethoxymethyl-[1,2,3]triazole and 5-[3-(Trifluoromethyl)phenyl]-4-(2-chloropyrimidin-4-yl)-1-ethoxymethyl-[1,2,3]triazole

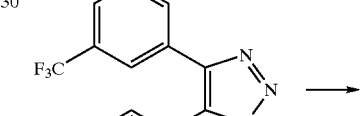

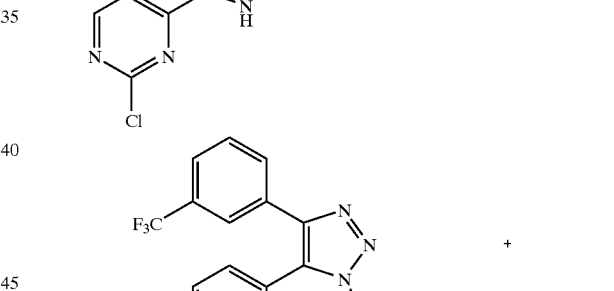

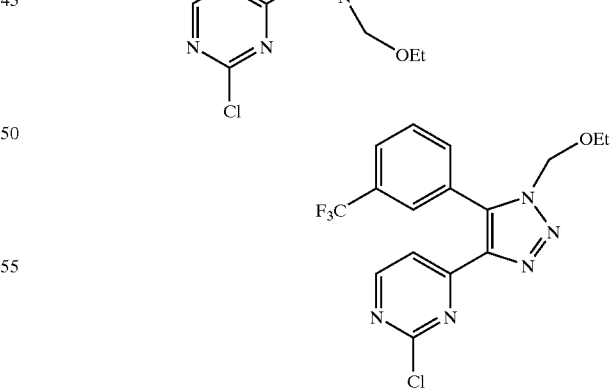

To a stirred solution of triazole 118a (1.11 g mg, 3.42 mmol) in CH₂Cl₂ (20 mL) is added chloromethyl ether (349 μL, 3.77 mmol) and triethylamine (340 μL, 2.44 mmol). The reaction is stirred at ambient temperature for 2 h, or until LC/MS of the crude reaction mixture shows complete conversion. The solution is then diluted with 0.1N HCl and extracted with CH$_2$Cl$_2$ three times. The combined organic phases are dried over MgSO$_4$, filtered and conc to dryness. The crude product is purified by prep HPLC to give two separable regioisomers (approximately 1:1) as slightly yellow solids. Note: regioselectivity is dependent upon reagents and reaction conditions.

c) 5-[3-(Trifluoromethyl)phenyl]-4-(2-phenoxypyrimidin-4-yl)-1-ethoxymethyl-[1,2,3]triazole

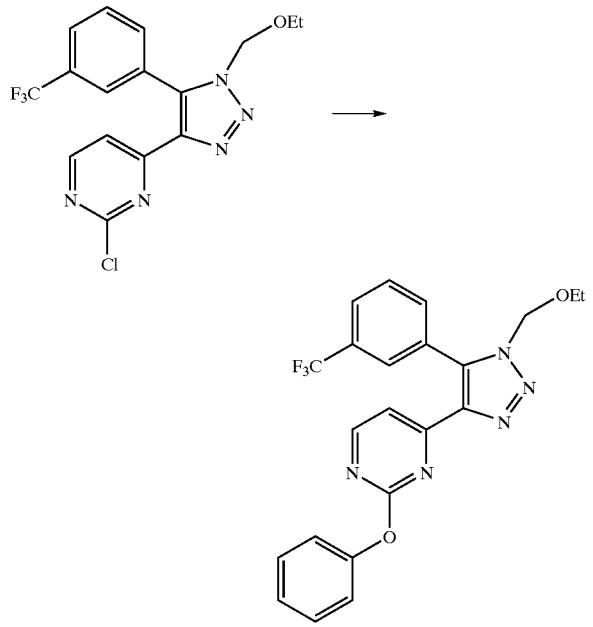

To a stirred solution of phenol (238 mg, 2.53 mmol) in tetrahydrofuran (4 mL) is added sodium hydride (60% dispersion, 76 mg, 1.90 mmol). After 5 min the suspension is transferred via syringe to a stirred solution of sulfoxide 118b (243 mg, 0.63 mmol) in tetrahydrofuran (4 mL). The reaction mixture is stirred overnight at ambient temperature, after which time the solution is diluted with H$_2$O and extracted with EtOAc three times. The combined organic layers are dried over MgSO$_4$, filtered and conc to dryness. The crude product is then purified by prep HPLC to give the desired product.

Examples 119–142 are prepared using substantially the same procedures as those described in Example 118, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 119–142 are illustrated by Table 7 below:

TABLE 7

| Example | Structure | Compound Name |
|---|---|---|
| 119 | (structure shown) | 4-(3-trifluoromethylphenyl)-5-[2-phenoxypyrimidin-4-yl]-1-ethoxymethyl-[1,2,3]triazole |

TABLE 7-continued

| Example | Structure | Compound Name |
|---|---|---|
| 120 | 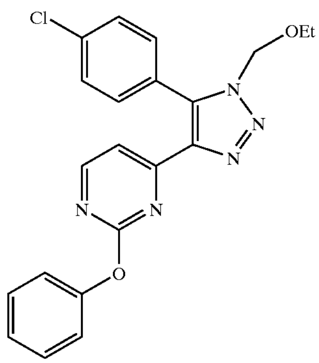 | 5-(4-chlorophenyl)-4-[2-phenoxypyrimidin-4-yl]-1-ethoxymethyl-[1,2,3]triazole |
| 121 | 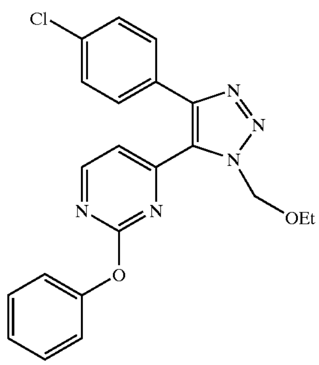 | 4-(4-chlorophenyl)-5-[2-phenoxypyrimidin-4-yl]-1-ethoxymethyl-[1,2,3]triazole |
| 132 | 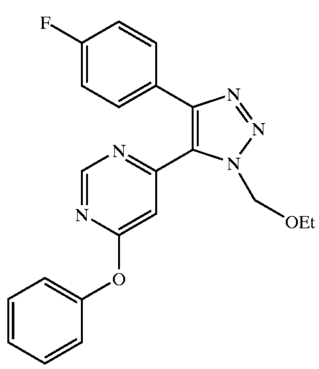 | 4-(4-fluorophenyl)-5-[4-phenoxypyrimidin-6-yl]-1-ethoxymethyl-[1,2,3]triazole |
| 133 | 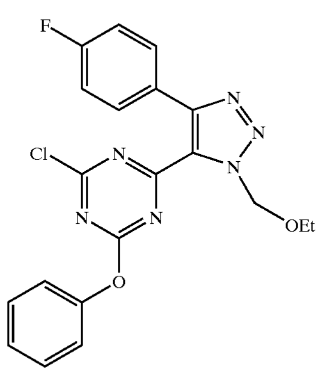 | 4-(4-fluorophenyl)-5-[2-chloro-4-phenoxytriazin-6-yl]-1-ethoxymethyl-[1,2,3]triazole |

TABLE 7-continued
| Example | Structure | Compound Name |
|---|---|---|
| 134 | 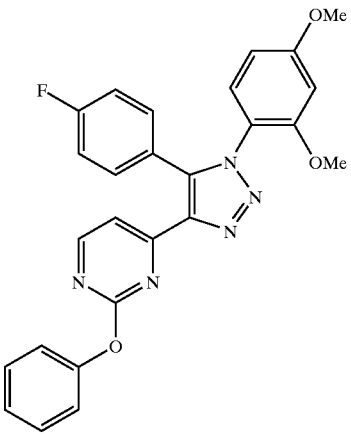 | 5-(4-fluorophenyl)-4-[2-phenoxypyrimidin-4-yl]-1-(2,4-dimethoxyphenyl)-[1,2,3]triazole |
| 135 | 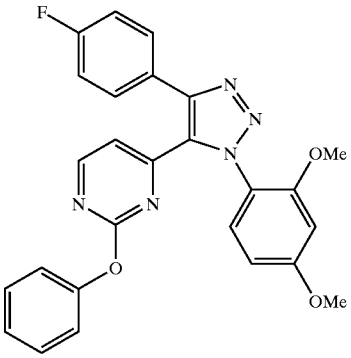 | 4-(4-fluorophenyl)-5-[2-phenoxypyrimidin-4-yl]-1-(2,4-dimethoxyphenyl)-[1,2,3]triazole |
| 136 | 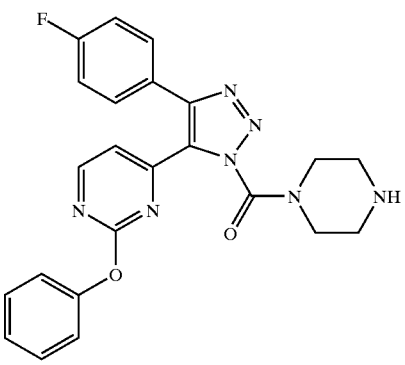 | 4-(4-fluorophenyl)-5-[2-phenoxypyrimidin-4-yl]-1-(piperidyl-N-carbonyl)-[1,2,3]triazole |
| 137 | 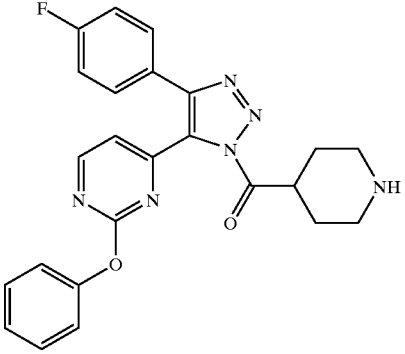 | 4-(4-fluorophenyl)-5-[2-phenyoxypyrimidin-4-yl]-1-(tetrahydrofuran-4-ylcarbonyl)-[1,2,3]triazole |

TABLE 7-continued

| Example | Structure | Compound Name |
|---|---|---|
| 138 | 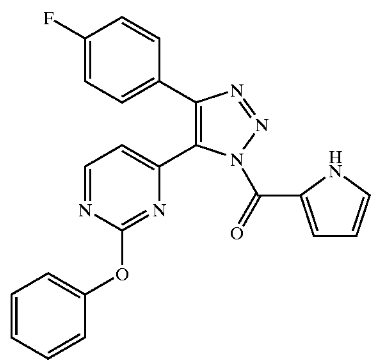 | 4-(4-fluorophenyl)-5-[2-phenoxypyrimidin-4-yl]-1-(pyrrol-2-ylcarbonyl)-[1,2,3]triazole |
| 139 | 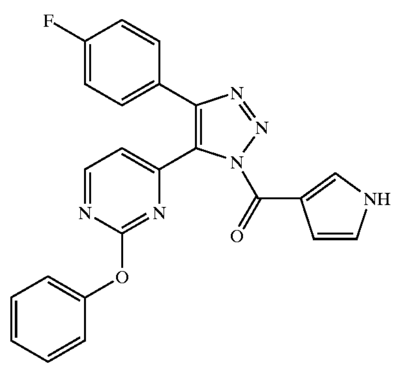 | 4-(4-fluorophenyl)-5-[2-phenoxypyrimidin-4-yl]-1-(pyrrol-3-ylcarbonyl)-[1,2,3]triazole |
| 140 | 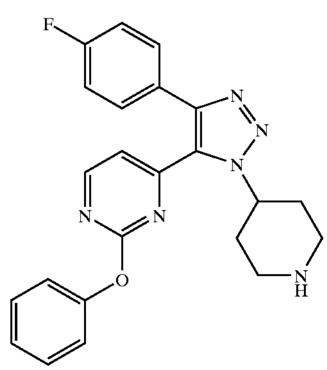 | 4-(4-fluorophenyl)-5-[2-phenoxypyrimidin-4-yl]-1-(tetrahydrofuran-4-yl)-[1,2,3]triazole |
| 141 | 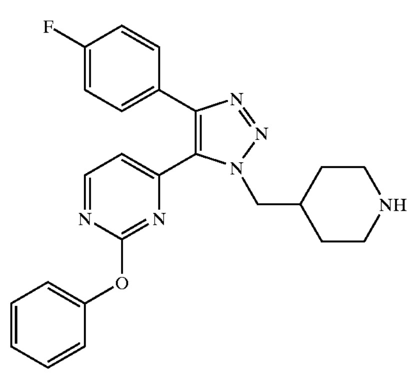 | 4-(4-fluorophenyl)-5-[2-phenoxypyrimidin-4-yl]-1-(tetrahydrofuran-4-ylmethyl)-[1,2,3]triazole |

TABLE 7-continued

| Example | Structure | Compound Name |
|---------|-----------|---------------|
| 142 | 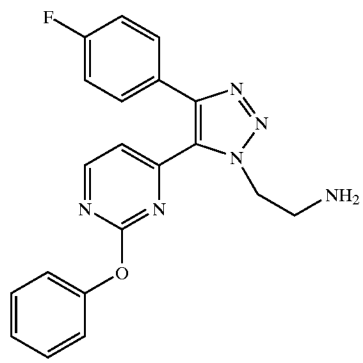 | 4-(4-fluorophenyl)-5-[2-phenoxypyrimidin-4-yl]-1-(2-aminoethyl)-[1,2,3]triazole |

Example 143

4-(4-Fluorophenyl)-5-[3-methyl-2-phenoxyimidazo-4-yl]-1-ethoxymethyl-[1,2,3]triazole a) 4-(4-Fluorophenylethynyl)-3-methyl-2-phenylthioimidazole p-Fluorophenyl acetylene and imidazole (Blass, B. E. et al. *Bio. Med. Chem. Lett.* 2000, 10, 1543–1545) are reacted according to published procedure (Mangalagiu, I. et al. *Acta Chem. Scand.* 1996, 50, 914–917) to give the desired alkyne as a brown solid which is used without further purification.

b) 4-(4-Fluorophenylethynyl)-3-methyl-2-phenylsulfonylimidazole

To a stirred solution of alkyne 143a (2.70 g, 8.7 mmol) in $CH_2Cl_2$ (70 ml) is added MCPBA (5.82 g 70%, 20.7 mmol). After 24 hours, the reaction is poured into 200 ml EtOAc, washed with $Na_2CO_3$ (3×50 ml), dried over $MgSO_4$, filtered and stripped to a solid. Chromatography with 3/1 hexane/EtOAc yields alkyne 143b as a white solid.

c) 4-(4-Fluorophenyl)-5-[3-methyl-2-phenylsulfonylimidazo-4-yl]-[1,2,3]triazole

Alkyne 143b is reacted with sodium azide as described for Example 86a to give the crude product as an oil. Chromatography with 1:1 hexane:EtOAc yields triazole 143c as a pale yellow solid.

d) 4-(4-Fluorophenyl)-5-[3-methyl-2-phenylsulfonylimidazo-4-yl]-1-ethoxymethyl-[1,2,3]triazole and 5-(4-Fluorophenyl)-4-[3-methyl-2-phenylsulfonylimidazo-4-yl]-1-ethoxymethyl-[1,2,3]triazole e) 4-(4-Fluorophenyl)-5-[3-methyl-2-phenoxyimidazo-4-yl]-1-ethoxymethyl-[1,2,3]triazole

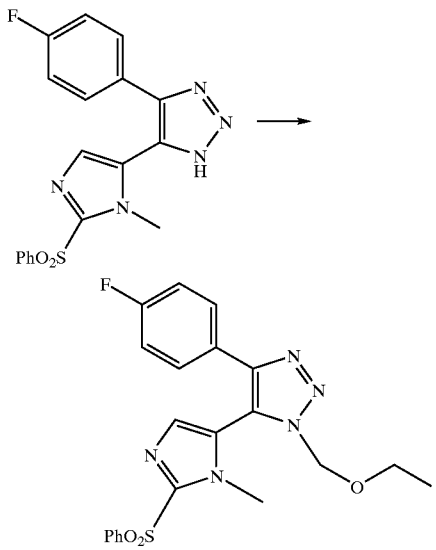

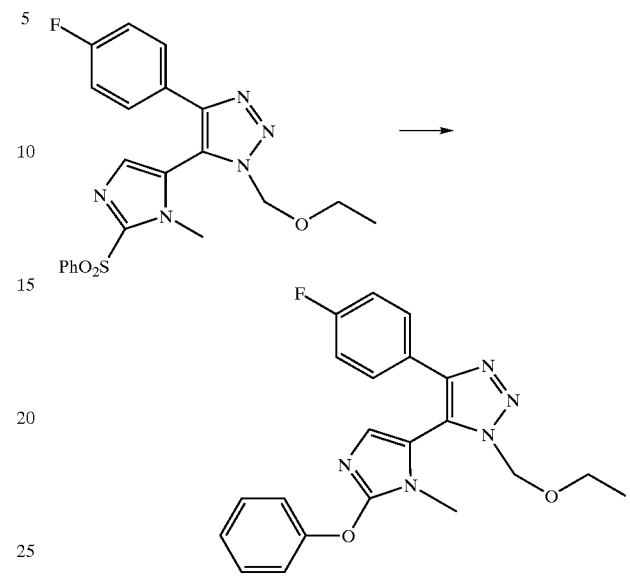

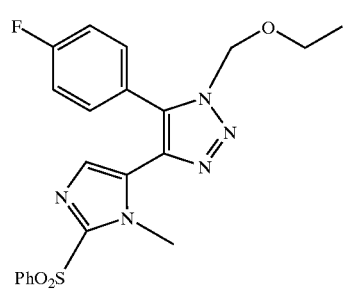

Triazole 143c is reacted with chloroethoxy methyl ether as described for Example 86b to give the crude product as an oil. Chromatography with 2:1 hexane:EtOAc yields the desired separable regioisomers as pale white solids.

Triazole 143d is reacted with sodium phenoxide as described for Example 86e to give the crude product as an oil. Chromatography with 60:40:0.8 hexane:EtOAc:MeOH provides 143e as a colorless oil.

Examples 144–146 are prepared using substantially the same procedures as those described in Example 143, substituting the appropriate starting materials. The skilled artisan may change temperature, pressure, atmosphere, solvents, or the order of reactions as appropriate. Additionally, the skilled artisan may use protecting groups to block side reactions or to increase yields as appropriate. All such modifications can be readily carried out by the skilled artisan in organic chemistry, and thus are within the scope of the invention.

Examples 144–146 are illustrated Table 8 below:

TABLE 8

| Example | | Compound Name |
|---|---|---|
| 144 | | 5-(4-Fluorophenyl)-4-[3-methyl-2-phenoxyimidazo-4-yl]-1-ethoxymethyl-[1,2,3]triazole |

TABLE 8-continued

| Example | | Compound Name |
|---|---|---|
| 145 | 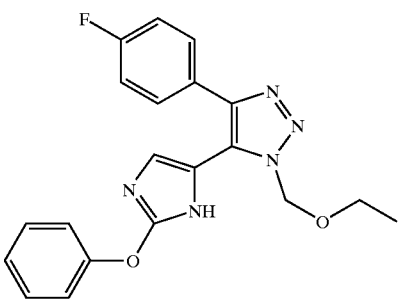 | 4-(4-Fluorophenyl)-5-[2-phenoxyimidazo-4-yl]-1-ethoxymethyl-[1,2,3]triazole |
| 146 | 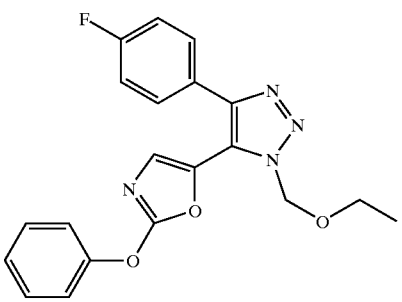 | 4-(4-Fluorophenyl)-5-[2-phenoxyoxazo-5-yl]-1-ethoxymethyl-[1,2,3]triazole |

Method of Use

As stated above, the compounds of the present invention are potent cytokine inhibitors. Accordingly, the compounds of Formula (I) or a pharmaceutically acceptable salt thereof can be used for the prophylactic or therapeutic treatment of diseases in humans or mammals that is associated with unwanted cytokine activity.

"Cytokine" as used herein refers to any secreted protein secreted by many different cell types involved in cell-to-cell communication and modulates interactions between cells in the inflammatory, immune or hematopoietic response. A cytokine includes, but is not limited to, monokines and lymphokines. Examples of cytokines include, but are not limited to, Interleukin-1 (IL-1), Tumor Necrosis Factor alpha and beta referred to collectively herein as (TNF), Interleukin-8 (IL-8) and Interleukin-6 (IL-6).

"Cytokine inhibition" as described herein, refers to: (i) a decrease of excessive in vivo levels of cytokines such as but not limited to IL-1, TNF, IL-6 and IL-8 to normal or sub-normal levels by inhibition of the in vivo release of the cytokines by all cells; (ii) a down regulation of the excessive expression of cytokine mRNA in vivo in a human to normal or sub-normal levels; (iii) a down regulation by inhibition of the direct synthesis of the cytokines such as but not limited to IL-1, TNF, IL-6 and IL-8 as a posttranslational event; or (iv) a down regulation, at the translational level, of excessive in vivo levels of cytokines such as but not limited to IL-1, TNF, IL-6 and IL-8 in a human to normal or sub-normal levels.

Compounds of Formula (I) are capable of inhibiting cytokines such as but not limited to IL-1, TNF, IL-6 and IL-8. These as well as other cytokines are important mediators of inflammation in a wide variety of diseases. The inhibition of these inflammatory cytokines is of benefit in treating many of these disease states. The invention also provides a method of treating a proteinase mediated disease in humans or mammals, wherein the production of the proteinase is affected by cytokines. Examples of such proteinases include but are not limited to the matrix metalloproteinases and disintegrin metalloproteases (ADAMs).

The ability of compounds of Formula (I) to inhibit TNF-α production is measured using lipopolysaccharide (LPS) stimulated human monocytic cells (THP-1) (See: (a) Mohler K. M., et al. "Protection against a lethal dose of endotoxin by an inhibitor of tumour necrosis factor processing" Nature 1994, 370, 218–220; (b) Regan J. R., et al. "Aromatic heterocyclic compounds as anti-inflammatory agents" WO 99/23091, PCT/US98/22907). Test compounds are incubated at various concentrations with THP-1 cells for 15 minutes before the stimulation of cytokine release by the addition of LPS (2 µg/mL). The amount of TNF-α released is measured 4 hours later using commercially available ELISA kits. The inhibition of TNF-α release by test compounds is measured by comparing to cultures treated with LPS and no test compound.

The compounds of Formula (I) are administered in a amount sufficient to inhibit cytokines such as but not limited to IL-1, TNF, IL-6 and IL-8, so that it is regulated to normal or subnormal levels, so as to prevent the disease state. The amount of cytokine considered abnormal for the present invention, constitute; levels of free cytokines such as but not limited to IL-1, TNF, IL-6 and IL-8 greater than or equal to 1 picogram per ml; any cell associated cytokines or; the presence of cytokine mRNA above basal levels in cells or tissues.

Therefore, these compounds are useful therapeutic agents for the treatment of diseases associated with unwanted cytokine activity including, osteoarthritis, rheumatoid arthritis, septic arthritis, psoriatic arthritis, rheumatic fever, gout, Reiter's syndrome, osteoperosis, diabetes, inflammatory bowel diseases including Crohn's disease and ulcerative colitis, pancreatitis, diverticulitis, sepsis, septic shock, toxic shock syndrome, respiratory diseases including asthma, chronic obstructive pulmonary disease (COPD), bronchitis, emphysema, cystic fibrosis, acute respiratory distress, fibrotic diseases of the lung and liver, diseases of the central nervous system such as Alzheimer's disease, amyotrophic lateral sclerosis (ALS), muscular dystrophy and multiple sclerosis, cachexia secondary to infection or malignancy and cachexia secondary to acquired immune deficiency syndrome.

Since cytokines can cause the overproduction of proteinases, the compounds of this invention are useful in preventing prosthesis loosening. It is known in the art that over time protheses loosen, become painful, and may result in further bone injury, thus requiring replacement. The need for replacement of such protheses includes those such as in, joint replacements (for example hip, knee and shoulder replacements), dental prosthesis, including dentures, bridges and prothesis secured to the maxilla and/ mandible.

Cytokines and proteinases are also active in remodeling in the cardiovascular system. It has been suggested that one of the reasons angioplasty has a higher than expected long term failure rate (reclosure over time) is that cytokine and proteinase activity is not desired or is elevated in response to what may be recognized by the body as "injury" to the basement membrane of the vessel. Similarly restenosis of surgical cardiovascular stents is thought to be mediated by cytokine induced proteinase production in response to "injury" induced by placement of the stent.

Compounds of this invention are also useful for the treatment of diseases which are caused by excessive or inappropriate angiogenesis. Such diseases, conditions or disorders include but are not limited to, various ocular diseases, such as macular degeneration and diabetic retinopathy, tumor growth and metastasis, atherosclerosis and rheumatoid arthritis.

In skin care, cytokines are implicated in the remodeling or "turnover" of skin. As a result, the regulation of cytokines improves treatment of skin conditions including but not limited to, wrinkle repair, regulation, prevention and repair of ultraviolet induced skin damage. Such a treatment includes prophylactic treatment or treatment before the physiological manifestations are obvious. For example, the cytokine inhibitor may be applied as a preexposure treatment to prevent ultraviolet damage and/or during or after exposure to prevent or minimize post-exposure damage. In addition, cytokines are implicated in skin disorders and diseases related to abnormal tissues that result from abnormal turnover such as epidermolysis bullosa, psoriasis, scleroderma and atopic dermatitis. The compounds of this invention are also useful for treating the consequences of "normal" injury to the skin including scarring or "contraction" of tissue for example, following burns and perhaps the regulation of hair growth.

Inhibition of cytokines are also thought to be useful for the treatment of ocular disorders (especially corneal ulceration, lack of corneal healing, macular degeneration and pterygium) gum disease (especially periodontal disease and gingivitis). Compounds preferred for, but not limited to, the treatment of ocular disorders, gum disease, and skin diseases may be administered topically.

Compositions

The compositions of the invention comprise:

(a) a safe and effective amount of a compound of the invention; and (b) a pharmaceutically-acceptable carrier.

As discussed above, numerous diseases are known to be mediated by excess or undesired cytokine activity. For example, these include osteoarthritis, rheumatoid arthritis, diabetes, HIV/AIDS, inflammatory bowel disease, chronic heart failure, hypertension, periodontitis and the like. Thus, the compounds of the invention are useful in the treatment or prevention of conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit cytokines at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

Modes of Administration

This invention also provides methods of treating or preventing disorders associated with excess or undesired cytokine activity in a human or other animal subject, by administering a safe and effective amount of a Formula (I) compound to said subject. The methods of the invention are useful in treating or preventing disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration.

The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the cytokine is accumulated by using targeting ligands. For example, to focus the inhibitors to cytokine contained in a specific cell type, the inhibitor is conjugated to an antibody or fragment thereof which is immunoreactive with a cellular marker as is generally understood in the preparation of immunotoxins in general. The targeting ligand can also be a ligand suitable for a receptor which is present on the target cell. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. For treatment of oral diseases, the compound may be applied locally in a gel, paste, mouth wash, or implant.

The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound selected from the group consisting of:

4-(4-Fluorophenyl)-5-pyridin-4-yl-1-(thiophen-2-ylcarbonyl)-[1,2,3]triazole 4-(4-Fluorophenyl)-5-pyridin-4-yl-1-methylcarbonyl-[1,2,3]triazole 4-(4-Fluorophenyl)-5-pyridin-4-yl-1-(furan-2-ylcarbonyl)-[1,2,3]triazole 4-(4-Fluorophenyl)-5-pyridin-4-yl-1-phenylcarbonyl-[1,2,3]triazole 4-(4-Fluorophenyl)-5-pyridin-4-yl-1-(2-methoxyphenylcarbonyl)-[1,2,3]triazole 4-(4-Fluorophenyl)-5-pyridin-4-yl-1-(3-methoxyphenylcarbonyl)-[1,2,3]triazole 4-(4-Fluorophenyl)-5-pyridin-4-yl-1-(4-methoxyphenylcarbonyl)-[1,2,3]triazole 4-(4-Fluorophenyl)-5-pyridin-4-yl-1-(2-chlorophenylcarbonyl)-[1,2,3]triazole 4-(4-Fluorophenyl)-5-pyridin-4-yl-1-(3-chlorophenylcarbonyl)-[1,2,3]triazole 4-(4-Fluorophenyl)-5-pyridin-4-yl-1-(4-chlorophenylcarbonyl)-[1,2,3]triazole 4-(4-Fluorophenyl)-5-pyridin-4-yl-1-ethoxycarbonyl)-[1,2,3]triazole 4-(4-Fluorophenyl)-5-pyridin-4-yl-1-(phenylthio-thiocarbonyl)-[1,2,3]triazole 4-(4-Fluorophenyl)-5-pyridin-4-yl-1-phenylmethoxycarbonyl-[1,2,3]triazole 4-(4-Fluorophenyl)-5-pyridin-4-yl-1-(2-methoxyethoxycarbonyl)-[1,2,3]triazole 4-(4-Fluorophenyl)-5-pyridin-4-yl-1-allyloxycarbonyl-[1,2,3]triazole 4-(4-Fluorophenyl)-5-pyridin-4-yl-1-[2-(phenylmethoxy)-ethoxycarbonyl)-[1,2,3]triazole 4-(4-Fluorophenyl)-5-pyridin-4-yl-1-methoxymethyl-[1,2,3]triazole 4-(4-Fluorophenyl)-5-pyridin-4-yl-1-ethoxymethyl-[1,2,3]triazole 4-(4-Fluorophenyl)-5-pyridin-4-yl-1-(2-chloroethoxymethyl)-[1,2,3]triazole 4-(4-Fluorophenyl)-5-pyridin-4-yl-1-[(2-methoxyethoxy)-methyl]-[1,2,3]triazole 4-(4-Fluorophenyl)-5-pyridin-4-yl-1-[(2-(benzoyloxy)-ethoxymethyl]-[1,2,3]triazole 4-(4-Fluorophenyl)-5-pyridin-4-yl-1-[(2-trimethylsilyl)-ethoxymethyl]-[1,2,3]triazole 4-(4-Fluorophenyl)-5-pyridin-4-yl-1-(2-chloro-1-ethoxyethyl)-[1,2,3]triazole 4-(4-Fluorophenyl)-5-pyridin-4-yl-1-pivalyloxymethyl-[1,2,3]triazole 4-(4-Fluorophenyl)-5-pyridin-4-yl-1-(phenylmethoxymethyl)-[1,2,3]triazole
4-(4-Fluorophenyl)-5-pyridin-4-yl-1-(2-methoxyethyl)-[1,2,3]triazole
4-(4-Fluorophenyl)-5-pyridin-4-yl-1-(2-ethoxyethyl)-[1,2,3]triazole
4-(4-Fluorophenyl)-5-pyridin-4-yl-1-(2-phenoxyethyl)-[1,2,3]triazole
4-(4-Fluorophenyl)-5-pyridin-4-yl-1-[2-(phenylmethoxy)-ethyl]-[1,2,3]triazole
4-(4-Fluorophenyl)-5-pyridin-4-yl-1-[2-(phenylcarbonyloxy)-ethyl]-[1,2,3]triazole
4-(4-Fluorophenyl)-5-pyridin-4-yl-1-[2-(2-ethoxyethoxy)ethyl)-[1,2,3]triazole
4-(4-Fluorophenyl)-5-pyridin-4-yl-1-methylsulfonyl-[1,2,3]triazole
4-(4-Fluorophenyl)-5-pyridin-4-yl-1-phenylsulfonyl-[1,2,3]triazole
4-(4-Fluorophenyl)-5-pyridin-4-yl-1-(2-methoxyphenylsulfonyl)-[1,2,3]triazole
4-(4-Fluorophenyl)-5-pyridin-4-yl-1-(3-methoxyphenylsulfonyl)-[1,2,3]triazole
4-(4-Fluorophenyl)-5-pyridin-4-yl-1-(4-methoxyphenylsulfonyl)-[1,2,3]triazole
4-(4-Fluorophenyl)-5-pyridin-4-yl-1-(4-chlorophenylsulfonyl)-[1,2,3]triazole
4-(4-Fluorophenyl)-5-pyridin-4-yl-1-(2-furansulfonyl)-[1,2,3]triazole
4-(4-Fluorophenyl)-5-pyridin-4-yl-1-(2-thiophenesulfonyl)-[1,2,3]triazole
4-(4-Fluorophenyl)-5-pyridin-4-yl-1-phenylaminocarbonyl-[1,2,3]triazole
5-(4-Fluorophenyl)-4-pyridin-4-yl-1-phenylaminocarbonyl-[1,2,3]triazole
4-(4-Fluorophenyl)-5-pyridin-4-yl-1-(N-ethyl-N-phenylaminocarbonyl)-[1,2,3]triazole
5-(4-Fluorophenyl)-4-pyridin-4-yl-1-(N-propyl-N-phenylaminocarbonyl)-[1,2,3]triazole
4-(4-Fluorophenyl)-5-pyridin-4-yl-1-(2,3, dihydro-indol-1-ylcarbonyl)-[1,2,3]triazole
5-(4-Fluorophenyl)-4-pyridin-4-yl-1-(2,3, dihydro-indol-1-ylcarbonyl)-[1,2,3]triazole
4-(4-Fluorophenyl)-5-pyridin-4-yl-1-(N,N-diphenylaminocarbonyl)-[1,2,3]triazole
4-(4-Fluorophenyl)-5-pyridin-4-yl-1-(carbazole-N-carbonyl)-[1,2,3]triazole
4-(4-Fluorophenyl)-5-pyridin-4-yl-1-(N,N-dimethylaminocarbonyl)-[1,2,3]triazole
4-(4-Fluorophenyl)-5-pyridin-4-yl-1-(N,N-diethylaminocarbonyl)-[1,2,3]triazole
4-(4-Fluorophenyl)-5-pyridin-4-yl-1-(N,N-di-isopropylaminocarbonyl)-[1,2,3]triazole
4-(4-Fluorophenyl)-5-pyridin-4-yl-1-(N,N-di-n-butylaminocarbonyl)-[1,2,3]triazole
4-(4-Fluorophenyl)-5-pyridin-4-yl-1-(tetrahydropyranyl-N-carbonyl)-[1,2,3]triazole
4-(4-Fluorophenyl)-5-pyridin-4-yl-1-(tetrahydrofuranyl-N-carbonyl)-[1,2,3]triazole
4-(4-Fluorophenyl)-5-pyridin-4-yl-1-(morpholino-N-carbonyl)-[1,2,3]triazole
4-(4-Fluorophenyl)-5-pyridin-4-yl-1-(piperidyl-N-carbonyl)-[1,2,3]triazole
4-(4-Fluorophenyl)-5-pyridin-4-yl-1-(N-methyl-N-phenylaminocarbonyl)-[1,2,3]triazole
4-(4-Fluorophenyl)-5-pyridin-4-yl-1-(phenylmethylaminocarbonyl)-[1,2,3]triazole
4-(4-Fluorophenyl)-5-pyridin-4-yl-1-[(4-methoxyphenyl)-methylaminocarbonyl]-[1,2,3]triazole
4-(4-Fluorophenyl)-5-pyridin-4-yl-1-[(4-chlorophenyl)-methylaminocarbonyl]-[1,2,3]triazole
4-(4-Fluorophenyl)-5-pyridin-4-yl-1-(3-chloropropylaminocarbonyl)-[1,2,3]triazole
4-(4-Fluorophenyl)-5-pyridin-4-yl-1-thiazol-2-yl-[1,2,3]triazole
4-(4-Fluorophenyl)-5-pyridin-4-yl-1-(phenyl)-[1,2,3]triazole
4-(4-Fluorophenyl)-5-pyridin-4-yl-1-(2-methylphenyl)-[1,2,3]triazole
4-(4-Fluorophenyl)-5-pyridin-4-yl-1-(4-methylphenyl)-[1,2,3]triazole
4-(4-Fluorophenyl)-5-pyridin-4-yl-1-(2-methoxyphenyl)-[1,2,3]triazole
4-(4-Fluorophenyl)-5-pyridin-4-yl-1-(3-methoxyphenyl)-[1,2,3]triazole
4-(4-Fluorophenyl)-5-pyridin-4-yl-1-(4-methoxyphenyl)-[1,2,3]triazole
4-(4-Fluorophenyl)-5-pyridin-4-yl-1-(3,4-dimethoxyphenyl)-[1,2,3]triazole
4-(4-Fluorophenyl)-5-pyridin-4-yl-1-(2,4-dimethoxyphenyl)-[1,2,3]triazole
4-(4-Fluorophenyl)-5-pyridin-4-yl-1-(benzo[1,3]dioxol-5-yl)-[1,2,3]triazole
4-(4-Fluorophenyl)-5-pyridin-4-yl-1-[4-(2-methoxyethoxy)-phenyl]-[1,2,3]triazole
4-(4-Fluorophenyl)-5-pyridin-4-yl-1-(4-phenoxyphenyl)-[1,2,3]triazole
4-(4-Fluorophenyl)-5-pyridin-4-yl-1-(4-ethoxyphenyl)-[1,2,3]triazole
4-(4-Fluorophenyl)-5-pyridin-4-yl-1-(4-trifluoromethoxyphenyl)-[1,2,3]triazole
4-(4-Fluorophenyl)-5-pyridin-4-yl-1-[4-(N,N-dimethylamino)-phenyl]-[1,2,3]triazole
4-(4-Fluorophenyl)-5-pyridin-4-yl-1-(4-bromophenyl)-[1,2,3]triazole
4-(4-Fluorophenyl)-5-pyridin-4-yl-1-(4-chlorophenyl)-[1,2,3]triazole
4-(4-Fluorophenyl)-5-pyridin-4-yl-1-(4-fluorophenyl)-[1,2,3]triazole
4-(4-Fluorophenyl)-5-pyridin-4-yl-1-(3-fluorophenyl)-[1,2,3]triazole
4-(4-Fluorophenyl)-5-pyridin-4-yl-1-(4-fluoro-2-methylphenyl)-[1,2,3]triazole
4-(4-Fluorophenyl)-5-pyridin-4-yl-1-(4-methylthiophenyl)-[1,2,3]triazole
4-(4-Fluorophenyl)-5-pyridin-4-yl-1-(4-methylsulfinylphenyl)-[1,2,3]triazole
4-(4-Fluorophenyl)-5-pyridin-4-yl-1-(4-methylsulfonylphenyl)-[1,2,3]triazole
4-(4-Fluorophenyl)-5-pyridin-4-yl-1-[4-(methoxycarbonyl)-phenyl]-[1,2,3]triazole
and 4-(4-Fluorophenyl)-5-pyridin-4-yl-1-(4-vinylphenyl)-[1,2,3]triazole.

\* \* \* \* \*